United States Patent [19]
Carroll

[11] Patent Number: 5,813,985
[45] Date of Patent: Sep. 29, 1998

[54] APPARATUS AND METHODS FOR PROVIDING ATTENUATION GUIDANCE AND TUMOR TARGETING FOR EXTERNAL BEAM RADIATION THERAPY ADMINISTRATION

[75] Inventor: Robert G. Carroll, Largo, Fla.

[73] Assignee: Care Wise Medical Products Corporation, Morgan Hill, Calif.

[21] Appl. No.: 509,627

[22] Filed: Jul. 31, 1995

[51] Int. Cl.⁶ ............................................ A61B 5/00
[52] U.S. Cl. .................................... 600/436; 600/1
[58] Field of Search .................. 364/413.24, 413.26; 128/653.1, 654, 659; 600/1, 436; 250/363.02, 363.07; 606/11; 607/89

[56] References Cited

U.S. PATENT DOCUMENTS

| | | | |
|---|---|---|---|
| 3,843,881 | 10/1974 | Barton, Jr. et al. | 250/269.1 |
| 3,936,646 | 2/1976 | Jonker | 250/363.1 |
| 4,150,289 | 4/1979 | Rosauer et al. | 378/56 |
| 4,340,818 | 7/1982 | Barnes | 378/155 |
| 4,419,585 | 12/1983 | Strauss et al. | 250/505.1 |
| 4,489,426 | 12/1984 | Grass et al. | 378/150 |
| 4,671,256 | 6/1987 | Lemelson | 128/654 |
| 4,682,604 | 7/1987 | Fymat et al. | 128/659 |
| 4,782,840 | 11/1988 | Martin, Jr. et al. | 128/654 |
| 4,801,803 | 1/1989 | Denen et al. | 250/336.1 |
| 4,873,632 | 10/1989 | Logan et al. | 250/363.02 |
| 4,893,013 | 1/1990 | Denen et al. | 128/659 |
| 4,932,412 | 6/1990 | Goldenberg | 128/654 |
| 4,949,365 | 8/1990 | Koike et al. | 378/54 |
| 4,959,547 | 9/1990 | Carroll et al. | 250/336.1 |
| 4,995,396 | 2/1991 | Inaba et al. | 128/654 |
| 5,036,210 | 7/1991 | Goodman | 235/493 |
| 5,039,867 | 8/1991 | Nishihara et al. | 250/492.3 |
| 5,068,883 | 11/1991 | DeHaan et al. | 378/86 |
| 5,148,040 | 9/1992 | Wise, Jr. et al. | 250/515.1 |
| 5,165,410 | 11/1992 | Warne et al. | 128/653.1 |
| 5,227,968 | 7/1993 | Ichihara | 364/413.24 |
| 5,339,347 | 8/1994 | Slatkin et al. | 378/65 |
| 5,438,202 | 8/1995 | Matanzon et al. | 364/413.24 |
| 5,520,182 | 5/1996 | Leighton et al. | . |
| 5,732,704 | 3/1998 | Thurston et al. | . |

OTHER PUBLICATIONS

"The Clinical Use of Radioactive Phosphorous", in the Annals of Surgery, vol. 130, pp. 643–651 (1949).

"A Miniaturized Probe For Detecting Radioactivity at Thyroid Surgery", in Physics In Medicine and Biology, vol. 15, pp. 397–404 (1971).

"Single Photon Scatter Compensation By Photopeak Energy Distribution Analysis", IEEE Transactions on Medical Imaging, vol. 11, pp. 161–164, Jun., 1992.

"A CSI—Crystal Surgical Scintillation Probe", in Nucleonics, vol. 14, pp. 102–108 (Nov. 1956).

*Primary Examiner*—William E. Kamm
*Assistant Examiner*—Carl H. Layno
*Attorney, Agent, or Firm*—Caesar, Rivise, Bernstein, Cohen & Pokotilow, Ltd.

[57] ABSTRACT

A system and method for providing external therapy radiation to radioactively tagged cancerous tissue via a radiation therapy machine. The system includes at least one radiation detector, e.g., a probe or gamma camera, and an analyzer, which is(are) arranged to be mounted with respect to the radiation therapy machine so that it(they) is(are) located adjacent the patient for receiving gamma rays and characteristic x rays emitted from the tagged cancerous tissue and for providing a signal representative thereof to the analyzer. The signal includes a first portion representing the characteristic x rays received from the tagged tissue and a second portion representing the gamma rays received therefrom. The portion of the signal corresponding to Compton-scattered photons is removed in the region of the full-energy gamma ray and in the region of the characteristic x ray. The analyzer uses selected portions of the signal to provide near-field information about the cancerous tissue, far-field information about the cancerous tissue, and extended field information about the cancerous tissue. This information is provided to the radiation therapy machine to control its operation so that it can irradiate the localized cancerous tissue from various directions to destroy the localized cancerous tissue, with minimal damage to adjacent viable normal tissue.

55 Claims, 16 Drawing Sheets

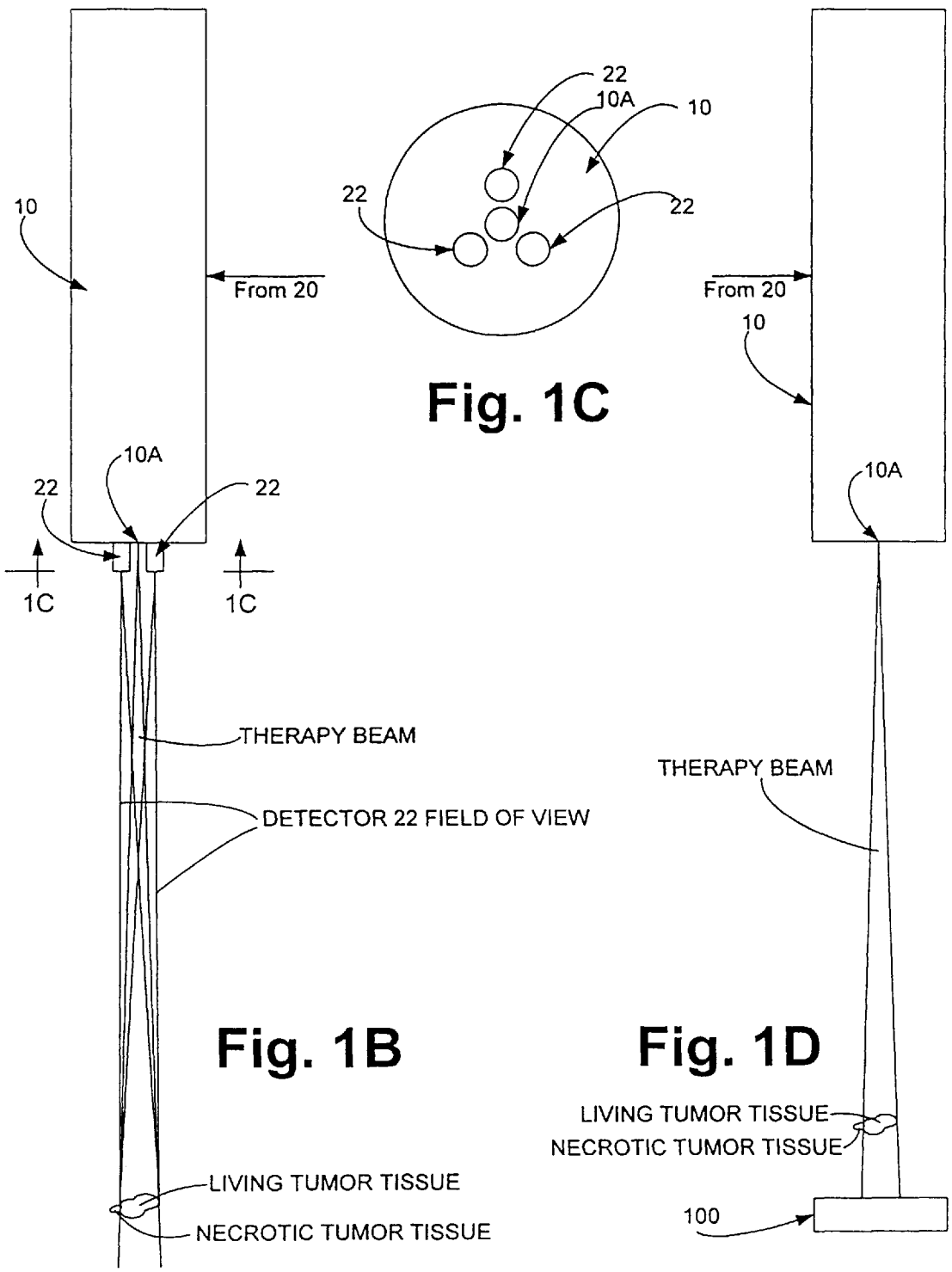

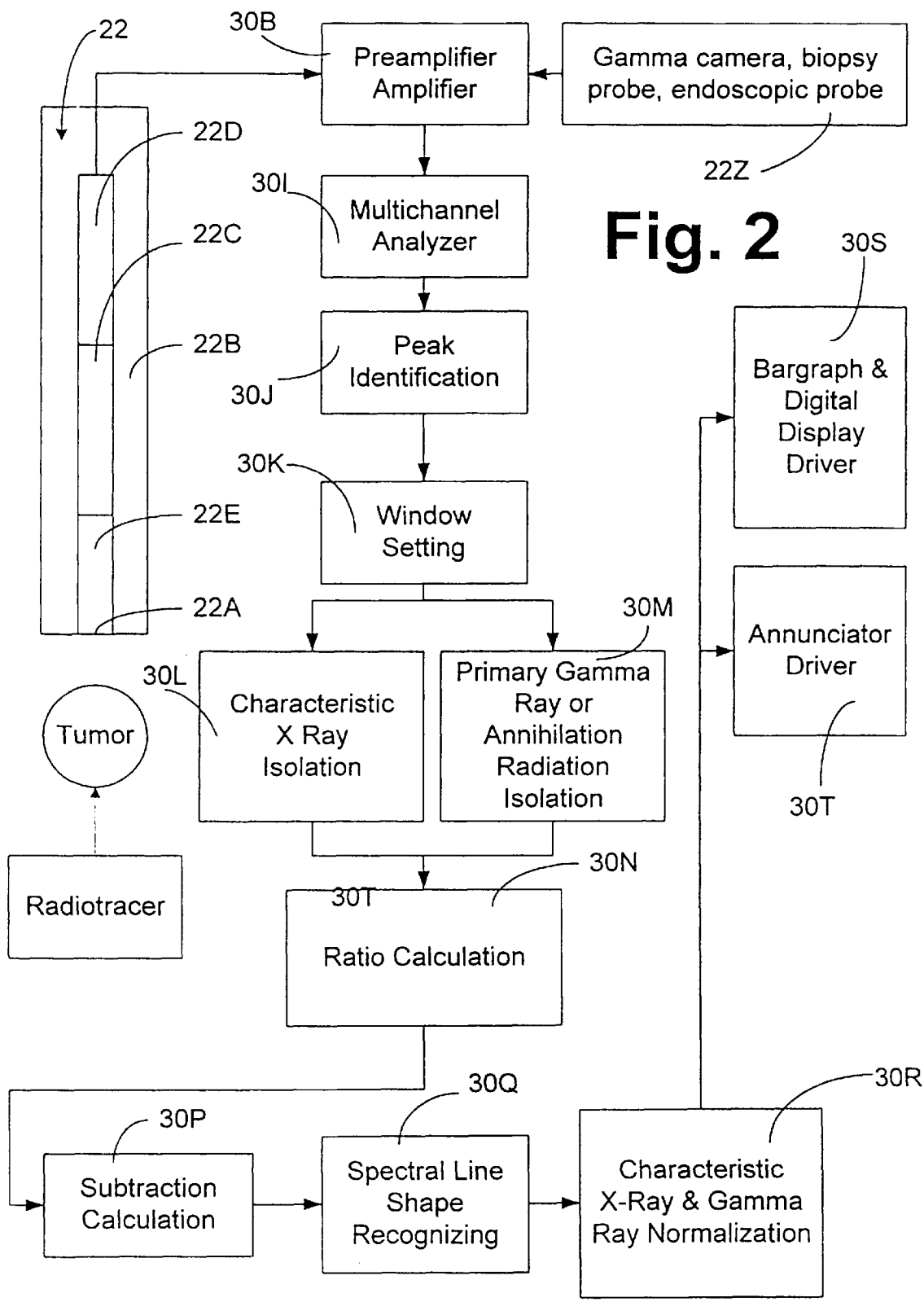

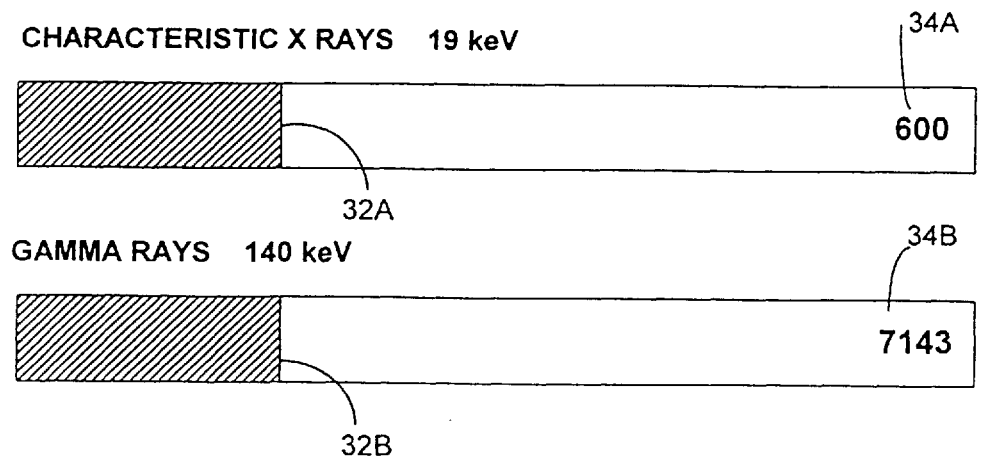
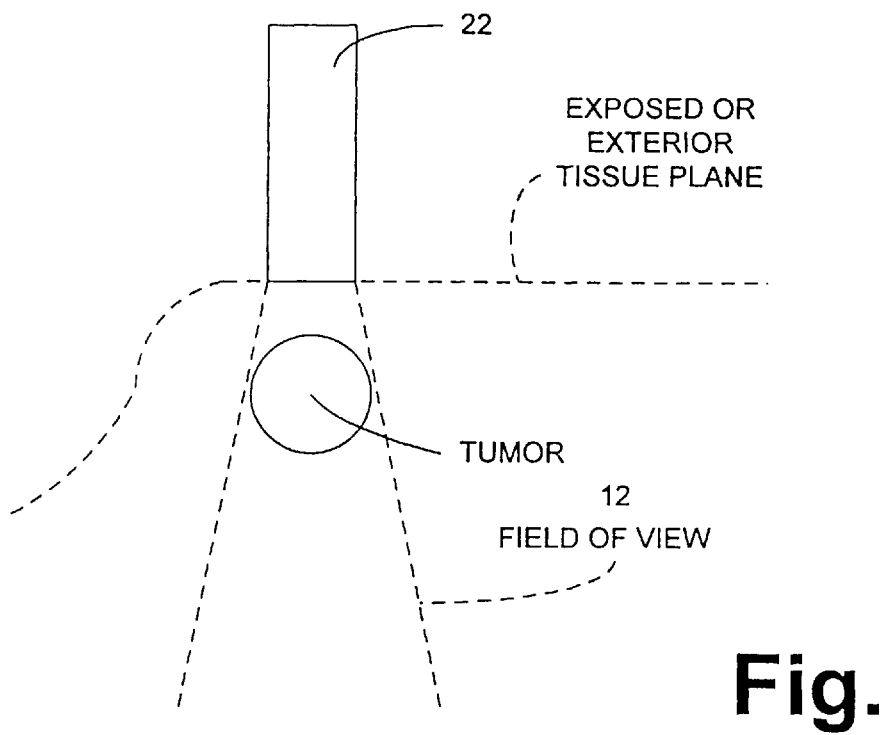
Fig. 3A

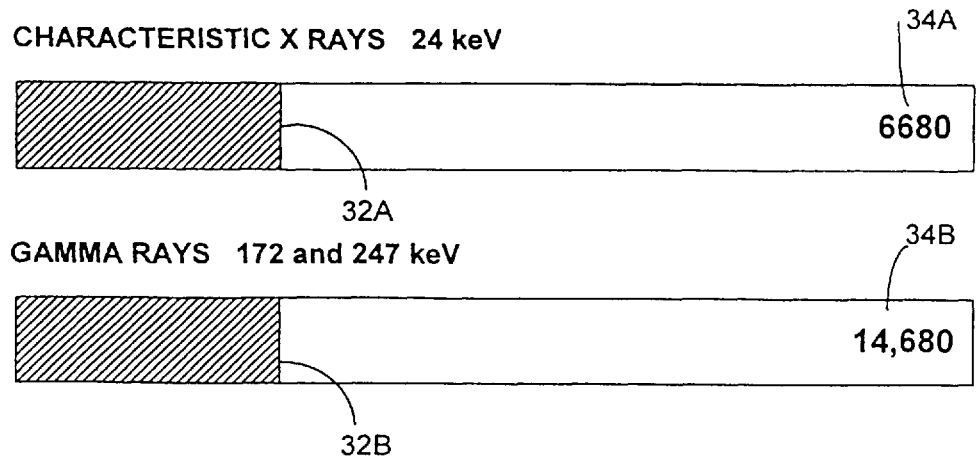
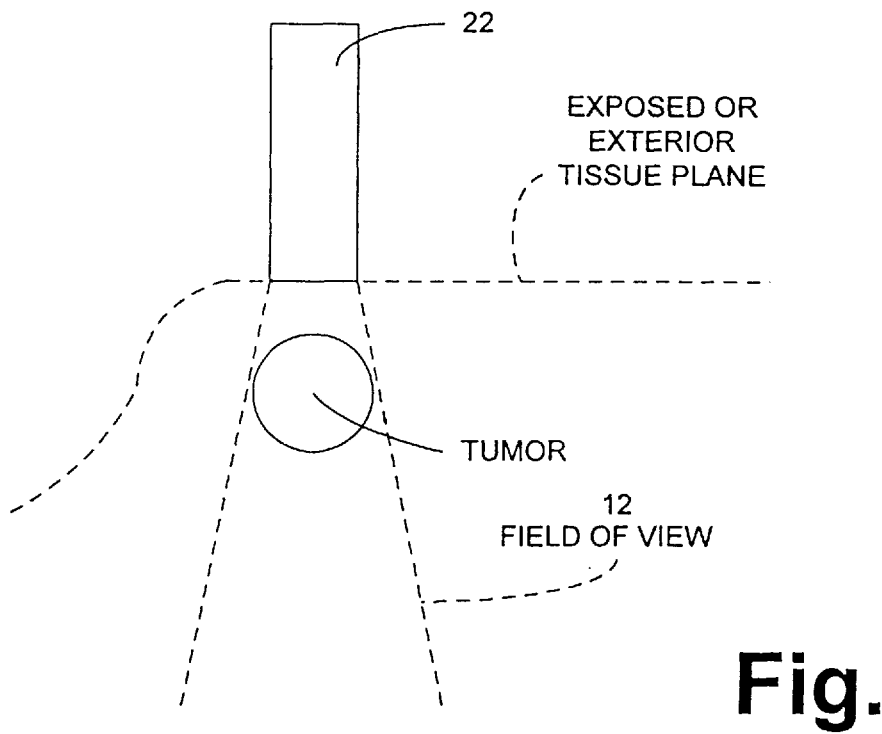
Fig. 3B

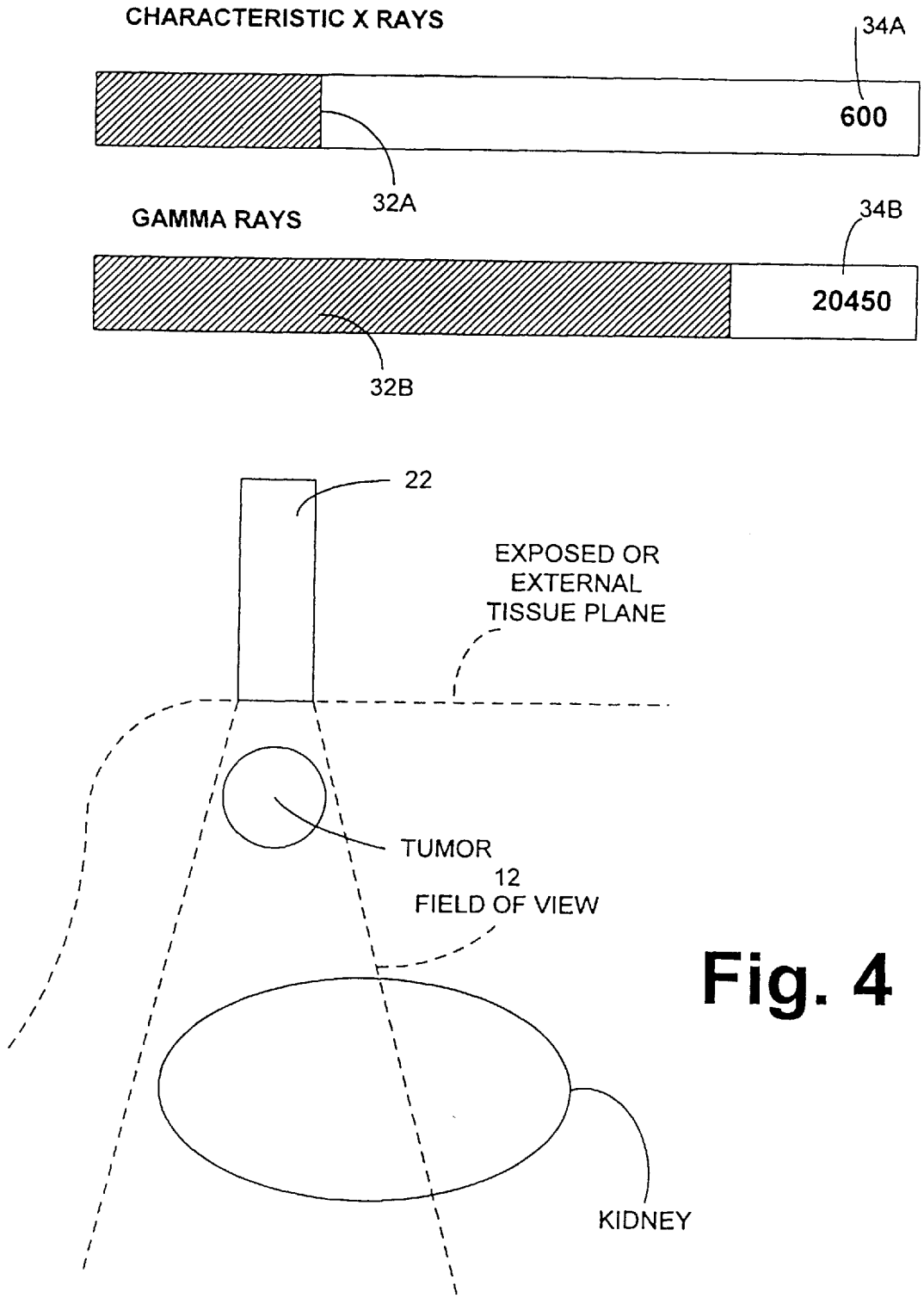

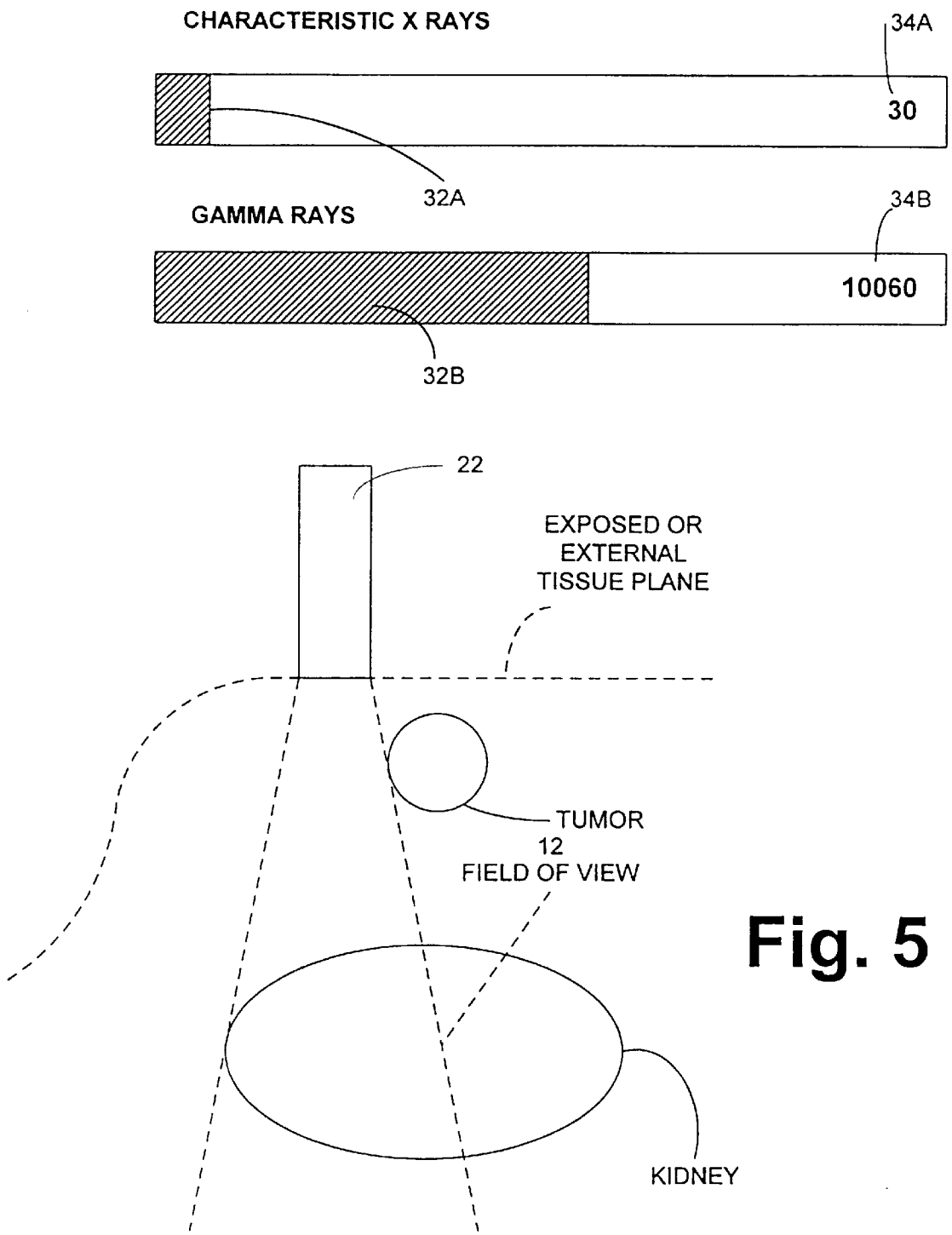

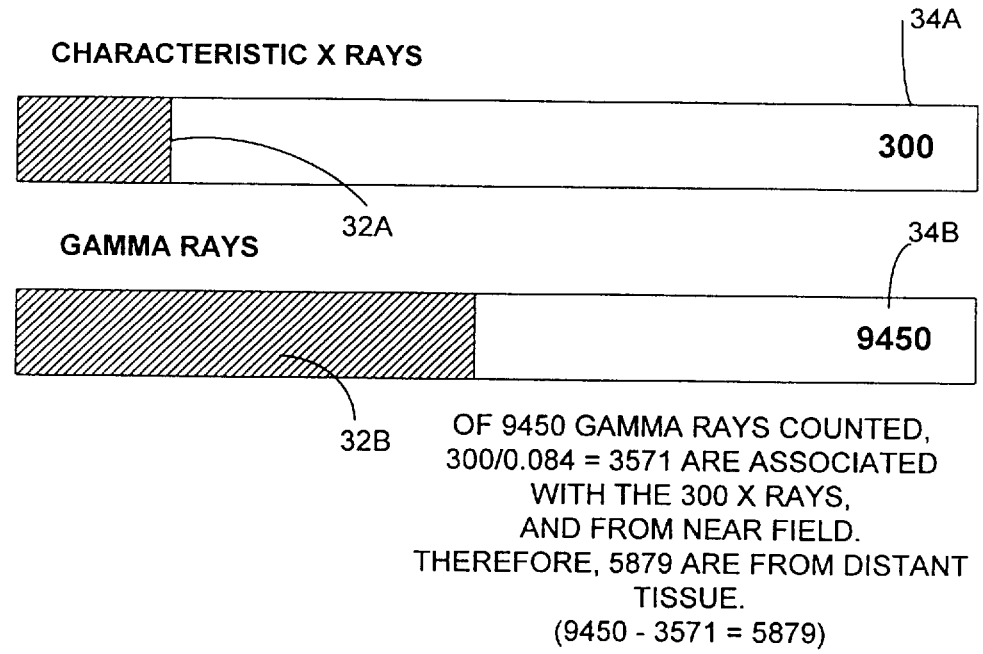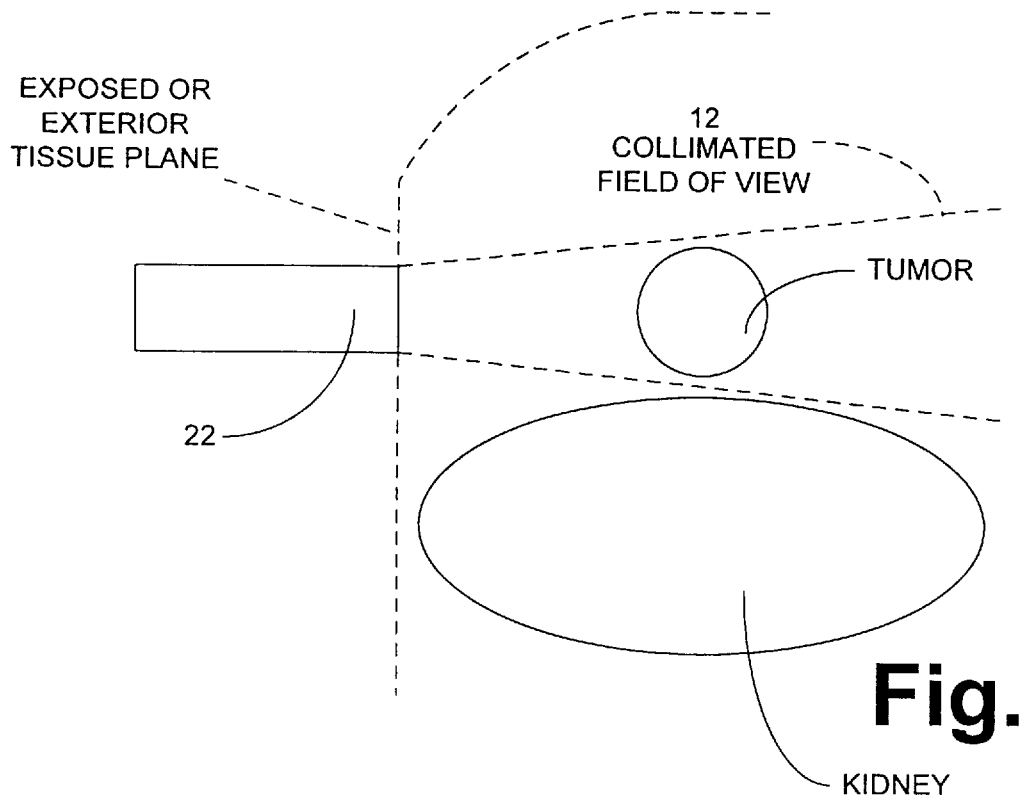
Fig. 9

APPARATUS AND METHODS FOR PROVIDING ATTENUATION GUIDANCE AND TUMOR TARGETING FOR EXTERNAL BEAM RADIATION THERAPY ADMINISTRATION

BACKGROUND OF THE INVENTION

This invention relates generally to apparatus and methods for providing radiation to tumors, and more particularly to providing external therapy radiation to living tumor tissue which has been localized by at least one tumor-localizing radiopharmaceutical. Examples of some specific apparatuses and methods to which this invention relates are: nuclear uptake probes for tumor targeting and attenuation guidance of intraoperative radiation therapy used in open surgical procedures and for guidance of conventional and specialized transcutaneous therapy, as well as nuclear medicine imaging cameras ("gamma cameras"), including those designed for operative use, and those employing solid state semiconductor detectors for tumor targeting and attenuation guidance.

The use of radioactive pharmaceuticals known as radiotracers to tag tissue within a patient for affecting the localization and demarcation of this tissue by radiation detecting devices including operative nuclear uptake probes has been disclosed in the medical literature for at least forty years. In the diagnosis and/or treatment of certain diseases, e.g., cancer, substances are introduced into the body that localize or identify diseased tissue, such as tumors, or other tissues of clinical interest (such as certain tumor bearing lymph nodes). Examples of such substances include Iodine 125, Iodine 131, Phosphorous 32, in appropriate solutions, which are themselves intrinsically radioactive. Other examples are materials such as Fluorine 18 deoxyglucose, monoclonal antibodies, peptides, and certain colloids, which have been labelled with radioactive isotopes. The combination of the tissue locating substance and the radioactive isotope (or "radioisotope") is referred to collectively as a radiotracer; similarly, the radioisotope which can itself localize in tissue of interest (e.g. Iodine 125) is also referred to as a radiotracer.

When injected intravenously, the radiotracer circulates throughout the body. Once the radiotracer encounters the target tissue cells, the radiotracer will adhere to or be absorbed (i.e. "be taken up") by those cells in concentrated amounts. Locations where radiotracers are taken up in concentrated amounts by the targeted tissue cells of clinical interest are known as areas of "specific uptake." Often only a small percentage, e.g., from less than one to five percent, of the total radiotracer injected will actually be taken up at the site of specific uptake. The remainder of the injected radiotracer will circulate to other regions and tissues of the body that are of no clinical interest, e.g., non-cancerous tissue, including circulating blood, and healthy bone marrow, liver and kidneys. The radioisotope of the radiotracer undergoes radioactive decay; that is, over time, the radioisotope experiences spontaneous nuclear transitions resulting in the emission of radiation, which typically includes gamma-ray photons and x-ray photons.

The radiotracer circulates and interacts with tissue and organs located throughout the body, such that these photons are emitted in random directions from locations that are of no clinical interest as well as from locations of specific uptake. Under prior art methods in nuclear medicine, practitioners are interested in detecting and evaluating gamma-ray photons that are emitted from the locations of specific uptake, while seeking to eliminate from the evaluation all photons emitted from sources that are of no clinical interest, e.g. non-cancerous tissue, circulating blood, and disease-free bone marrow, liver, and kidneys.

The energies of the gamma-ray photons emitted by the radioisotopes are unique to each isotope. At the time of their creation, these gamma rays are termed "full energy" or "primary" gamma rays. For the emitted photon to have enough energy to exit the patent's body in sufficient quantities to be able to form an image in a gamma camera, its energy must be above about 60 kev. For radiotracers in common use, the gamma-ray energies may be as high as about 511 keV. As an example, when Technetium 99m, an isotope often used in nuclear medicine, decays, 89% of the time a full-energy 140-keV gamma ray is emitted. Natural abundance ("abundance") or yield refers to the percentage of time that a decay or disintegration of the radioisotope nucleus results in production of the photon of interest, in this case the 140-keV full-energy gamma-ray photon. Indium 111, another commonly used radioisotope, emits 172-keV full-energy gamma rays, with an abundance of 89.6%, and 247-keV full-energy gamma rays, with an abundance of 93.9%. Fluorine 18 emits a positron which promptly interacts with an electron, thus yielding two 511 keV rays. Most of these gamma-ray emitting radioisotopes also emit characteristic x rays. The characteristic x rays originate in the following way. When the nucleus undergoes radioactive decay, an electron is sometimes removed from one of the orbital shells, most often the inner orbital shell. An electron from one of the outer orbital shells promptly falls back to the inner shell to take the place of the ejected electron so that the atom returns to its ground state. This action results in the emission of a characteristic x ray. The emitted x ray is described as "characteristic" because its energy is characteristic of the specific element involved. Characteristic x-ray emissions from radioisotopes used in nuclear medicine are typically of low energies i.e., from about 15 to 30 keV. For example, the radioactive decay of Technetium 99m results in Technetium characteristic x rays of about 19 keV, with an abundance of 7.5%, in addition to the 140 keV gamma ray previously discussed. The radioactive decay of Indium 111 results in Cadmium characteristic x-rays of approximately 24 keV, with an abundance of 83.5%.

The ratio of the number of full-energy gamma rays to the number of characteristic x rays emitted by each radioisotope is fixed and known, and reflected in the related abundance figures.

Under prior art methods in nuclear medicine, practitioners have typically utilized either the full-energy gamma rays alone in determining the location of cancerous or other tissues of interest in one instance, the combined signal from detection of both x rays and gamma rays together, without separately measuring and comparing the two signals, is being used. This is being done in the NEOPROBE device, made by Neoprobe Corporation of Columbus, Ohio. The NEOPROBE device detects both the 27-keV x rays and 35-keV gamma rays from Iodine 125.

There are several factors that make the evaluation of full-energy gamma-ray photons difficult. These factors have tended to make the detection and evaluation of the characteristic x rays even more difficult. Other than in the NEOPROBE device mentioned above, practitioners have seldom utilized the characteristic x rays and largely have not recognized the utility of the characteristic x ray in nuclear medicine. No practitioners have utilized the separate signals from characteristic x rays and the separate signals from gamma rays, and compared them to each other, in order to determine the spatial coordinates of tissue with nuclear uptake, or of the density of intervening tissue. Some of the problems associated with the use of both full-energy gamma rays and characteristic x rays, together and separately, to locate tissues of interest are discussed below.

Soft tissue in the human body is largely water, with small admixtures of light elements. Therefore soft tissue, blood, and most tumors have similar densities, approximately that of water. Bone is much denser, while lungs, because of their large air content, have effective densities much less than water. The probability of photons being absorbed as they move through matter is exponential. Gamma rays with energies from 60 to 500 keV usually travel relatively long distances before absorption in soft tissue (several hundred millimeters), whereas characteristic x rays of about 20 to 30 keV usually travel substantially shorter distances (30 millimeters or less). Consequently, these x rays cannot create images in gamma cameras because they are virtually all absorbed by fat, muscle, and skin. Such absorption is a measure of the thickness of tissue.

Furthermore, as previously mentioned, in addition to being taken up in tissue of clinical importance, imaging radiotracers may also be taken up in tissues and body fluids, such as blood, that are not of clinical interest. In the instance of Indium-111 labeled cancer-seeking antibodies, for example, a twenty-gram tumor may have only one percent of the total injected radiopharmaceutical dose, whereas the liver may have thirty five percent of the injected dose, on a non-specific basis (i.e., with no cancer present in the liver). The number of detected full-energy gamma rays from said liver, as measured by a hand-held nuclear uptake probe, may be from ten to one hundred times greater than those from the tumor. Significant radiation activity may also persist in circulating blood and in disease-free bone marrow throughout the body. As another example, Technetium 99m-labeled antibodies often show strong nonspecific uptake in the kidneys. This non-specific uptake in tissues which are not of clinical interest is an important source of background radiation.

The photons that lose energy and change direction due to the process known as Compton scattering represent additional background radiation. Compton scattering takes place when a photon interacts with an electron, and thereby loses energy and changes direction. The Compton scattering which results from the interaction of incident gamma photons with electrons of body tissues creates a virtual sea of scattered photons having energies ranging from slightly below the full-energy gamma-ray photons down to and below typical x ray energies ("the Compton continuum"). The directions, and thus the apparent points of origin of these Compton-scattered photons have only a limited relationship to the site from which the original, unscattered, full-energy gamma rays originated, and therefore have little relationship to the location of the tissue of interest.

The widespread distribution of radiotracers often encountered in tissues which are not of clinical interest described above, including the relatively high preferential uptake in certain organs, plus the additional radiation from Compton-scattered photons contributes to nonuniform and sometimes very intense levels of non-specific background radiation.

Under prior art methods, these marked variations in background radiation, including misleading signal from organs with no disease but high uptake, plus the abundant, almost randomly- directed Compton-scattered photons have seriously compromised the search for specifically labelled tissue with hand-held probes and with gamma cameras.

Further, the Compton-scattered photons add background radiation and compete for processing time with signal corresponding to unscattered gamma rays and x rays.

There are additional drawbacks associated with prior art methods of detecting full-energy gamma ray photons. The attenuation by body tissues of full-energy gamma-rays from very small tumors located deep within the patient's body have resulted in an inability of gamma cameras to locate many such sites. This problem is made more severe because some tumors simply fail to take up enough radiotracer to be detected at a distance. Since 1949 operative nuclear uptake probes have been used by surgeons in an effort to overcome these drawbacks.

Prior art hand-held nuclear uptake probes can be classified into two categories, contact probes and extended-range probes. Contact probes have been used to detect radiation having a short range, such as electrons and positrons from beta decay, and relatively low energy photons (i.e., below 60 keV). Examples are the 27-keV x rays and 35-keV full-energy gamma rays of Iodine 125. These contact applications are characterized by significant reduction in the number of full-energy photons detected due to the absorption and/or scattering of the radiation that occurs in overlying or commingled tissue of only a few millimeters depth. Consequently, contact probes are limited to applications wherein the probe is essentially in contact with the radio-labelled tissue of interest. This limitation is an advantage in situations of modest specific tissue uptake coupled with high non-specific background radiation from underlying tissue, such as is the case with some radiolabelled monoclonal antibodies. Such contact probes share features of excellent localization when radiolabels are used that emit only lower energy photons with short ranges in tissue, as in the case with Iodine 125. However, gamma camera images cannot be obtained of tissues labeled with radiotracers that emit only short-ranged radiation, as mentioned earlier. Further, it is difficult to use such contact nuclear uptake probes to scan tissues for radiolabeled sites of unknown depth.

As reported in an article entitled "The Clinical Use Of Radioactive Phosphorous", in the Annals of Surgery, Vol. 130, pps. 643–651 (1949), by Selverstone, Sweet, and Robinson, those authors used a contact hand-held nuclear uptake probe to determine boundaries of resection in a glioblastoma multiforme. They used Phosphorus-32 which emits a beta particle. These were detected with a blunt needle Geiger-Mueller detector. In this instance signal-to-noise ratio was excellent because the normal brain has an intact blood brain barrier which excludes Phosphorus. The short range of about one millimeter of the Beta particle in tissue obviated background from bone marrow as well as from more distant sources. No use of characteristic x rays and gamma rays was made by Selverstone, et al.

The use of extended-range nuclear uptake probes was reported by Craig, Harris, et al, in an article entitled "A CSI—Crystal. Surgical Scintillation Probe", in Nucleonics, Volume 14, pps. 102—108 (November 1956). In a case of post-operative residual tissue, tissues labelled with Iodine 131, which emits full-energy 364-keV gamma rays, were localized using a Cesium Iodide scintillation-crystal-based hand-held nuclear uptake probe. This probe used a light pipe to transmit the scintillation signal to a photomultiplier tube. The very high physiological concentration of Iodine 131 by the thyroid provided large numbers of detected photons while absent of other Iodine concentrations in the neck minimized background radiation. Shielding and collimation were used to minimize detection of background radiation from Iodine 131 in the gastric mucosa. In 1971, A. C.

Morris, T. R. Barclay, A. Tanida, et al. reported on using a transistorized version of this CsI probe in an article entitled "A Miniaturized Probe For Detecting Radioactivity At Thyroid Surgery", in Physics In Medicine And Biology, Volume 15, pps. 397–404 (1971).

Under conditions of high uptake in the tissue of interest, rapid blood pool clearance, and low non-specific uptake, probe localization of radiolabelled tissues can be relatively easy. Current Technetium 99m sulfur colloid lymph node mapping techniques for finding the sentinel node in melanoma and breast cancer approach this ideal. Imaging provides a map of the actual anatomic distribution of lymph node drainage patterns, while the probe readily finds small nodes deep in fat and other tissue.

Many radiotracers are far from ideal for probe use because of limited tumor-to-background contrast, abundant far-field non-specific uptake, and slow blood pool clearance relative to the physical half life of the radioisotope. Indium 111 labelled monoclonal antibodies, such as Oncoscint® marketed by Cytogen Corporation, has about 0.05% injected dose per gram of tumor. The signal from this low does competes with that from about 35% of the dose in the 1800 gram liver. As mentioned previously, this can result in full-energy gamma rays from said liver, as measured by a hand-held nuclear uptake probe, being from ten to one hundred times greater than those from the tumor.

There is also significant uptake in the bone marrow, and in circulating blood. On Nuclear Medicine scans, tumor is about the same density as imaged large blood vessels, which are commonly immediately adjacent to tumor involved lymph nodes.

Neoprobe Corporation provides a device for a method wherein a tumor-seeking monoclonal antibody is tagged with the radioactive isotope Iodine-125 and injected into the body to determine the location of cancerous tissue. See U.S. Pat. Nos. 4,782,840, 4,801,803, and 4,893,013. Iodine 125, whose half-life is 60 days emits a full-energy 35-keV gamma-ray at the low energy of 35 keV and a 27-keV characteristic x-ray. These photons are detected in a single broad energy window by the practitioner during surgical exploration with the use of a hand-held contact nuclear uptake probe. The relatively long half-life of 60 days (i.e., long compared to that of many other imaging nuclear medicine radioisotopes) allows the practitioner to wait until much of the radiotracer has been biologically cleared from the blood pool and the background radiation has been much reduced. However, this process reportedly takes about three weeks, and thus causes a corresponding delay of surgery. This delay is considered by some practitioners to be a disadvantage. In addition, the low energy photons can not be used for preoperative imaging by gamma cameras. If a Technetium-99m bone scan or Indium-111 white cell scan is done close to the scheduled date of surgery, background radiation arising from Compton scattering of full-energy gamma rays emitted by Technetium or Indium can make Iodine-125 localization extremely difficult. The NEOPROBE device uses a single energy "window" or band wide enough to include both the 27-keV characteristic x ray and the full-energy 35 keV gamma ray, and thus cannot distinguish between these two photons.

Other techniques employed with hand-held surgical nuclear uptake probes to deal with background radiation have included: control measurements of uptake of adjacent tissues, using identical probe angular orientation; aiming the probe consistently away from all organs with high non-specific uptake, with extended-field probes; use of a hand-held or hand-placed radiation blocking plate, with extended-field probes; use of a "window" which limits the photons measured by the radiation-detecting system to those of energies close to that of the full-energy gamma-ray peak; and the use of collimation appropriate to the size and also the depth of the lesion.

Operative nuclear uptake probes augmented by radiation blocking plates and selectable collimation are the subjects of U.S. Pat. Nos. 5,148,040, 4,959,547, and 5,036,210.

While each of these techniques has markedly reduced the problems caused by non-specific background radiation, there are circumstances in which one or more of these techniques can not be easily employed, the methods are sometimes time-consuming, or a high degree of familiarity and specific experience is required of the practitioner.

For example, extended-field probes are challenged by applications involving Indium-111 labelled antibodies. About 35 percent of the activity can be from non-specific liver uptake. Tumor activity is often diffusely present throughout the bone marrow, and the tumor activity per gram is often similar to that found in circulating blood. Despite techniques such as aiming the probe to avoid sites of known high non-specific uptake, use of selectable collimation, and use of a radiation-blocking plate where anatomically possible, the acquisition of good intraoperative skills by the practitioner can be very time-consuming.

Contact probes, on the other hand, are severely limited by attenuation by overlying tissue of only a few centimeters thickness. The tissue of interest, such as a tumor, must be almost completely exposed and essentially in contact with the probe in order for the probe to detect the uptake. Consequently, it is difficult to use contact nuclear uptake probes to scan tissues for radiolabelled sites of unknown depth, or, for example, to explore for retroperitoneal nodes during colorectal procedures without surgically penetrating the peritoneum. Gamma camera images cannot be obtained using many of the radioisotopes used with contact probes, such as Iodine-125.

Compton-scatter correction for gamma camera imaging has been discussed in various articles. See for example, K. W. Logan and W. D. McFarland, "Single Photon Scatter Compensation By Photopeak Energy Distribution Analysis", IEEE Transactions on Medical Imaging, Vol. 11, pps. 161–164, June 1992. U.S. Pat. No. 4,873,632 (Logan et al.) discloses a system utilizing filtering to reduce background radiation introduced by Compton-scatter in imaging by means of a gamma camera.

U.S. Pat. No. 3,843,881 (Barton) discloses a method for detecting the presence of metals in subterranean formations. Under Barton, a formation is irradiated with high energy electromagnetic radiation from a suitable source, such as radioactive material. Characteristic x rays are emitted from the metals as the result of being irradiated. These x rays are detected and measured to provide information regarding the presence and type of metal ore in the formation. Barton does not disclose the measuring and comparing of the gamma ray to a characteristic x ray to determine lateral location and depth of radiolabelled objects, or depth of intervening material. Further, Barton does not make use of the display of gamma-ray or x-ray photons stripped of the display of radiation from Compton-scattered photons.

U.S. Pat. No. 4,949,365 (Koike) describes an apparatus for measuring the density of objects such as bones, by transmitting gamma rays having different energy levels. Koike does not make use of characteristic x rays and/or full-energy gamma rays for the measuring spatial coordinates. Further, Koike does not make use of the display of gamma-ray or x-ray peaks stripped of the display of radiation from Compton-scattered photons.

U.S. Pat. No. 3,936,646 (Jonker) describes a focusing collimator kit with multiple stackable components for isotope imaging. This patent does not disclose the use of combined characteristic x rays and gamma rays in the determination of spatial coordinates of the tissue detected, or of the density of intervening tissue. Further, Jonker does not make use of the display of gamma-ray or x-ray peaks stripped of the display of radiation from Compton-scattered photons.

U.S. Pat. No. 4,150,289 (Rosauer) describes a gamma-ray inspection system for measuring the wall thickness of a tubular product, and in particular an associated calibration block. This patent does not disclose the combined use of characteristic x rays and gamma rays in the determination of spatial coordinates of the material detected, or of the density of intervening material. Further, Rosauer does not make use of the display of gamma-ray or x-ray peaks stripped of the display of radiation from Compton-scattered photons.

U.S. Pat. No. 4,340,818 (Barnes) describes a scanning grid apparatus used in x-ray radiology that provides improved transmissivity of full-energy x rays passing through the subject while providing reduced scatter radiation penetration. This patent does not disclose the combined use of both characteristic x rays and full-energy gamma rays in the determination of spatial coordinates of the tissue detected, or of the density of intervening material. Further, Barnes does not make use of the display of radiation from Compton-scattered photons.

U.S. Pat. No. 4,419,585 (Strauss) describes a variable angle radiation collimator used in a gamma camera system for radiological examination of human subjects. The collimator proves collimation of gamma rays so as to transmit radiation in a predetermined orientation. This patent does not disclose the combined use of both characteristic x rays and full-energy gamma rays in the determination of spatial coordinates of the tissue detected, or of the density of intervening tissue. Further, Strauss does not make use of the display of gamma-ray or x-ray peaks stripped of the display of radiation from Compton-scattered photons.

U.S. Pat. No. 4,489,426 (Grass) describes a collimator for regulating the shape and size of the pattern of radiation projected on a radiation detector from a radiation source, particularly for regulating the beam of radiation in a medical diagnostic x-ray machine. This patent does not disclose the combined use of both characteristic x rays and full-energy gamma rays in the determination of spatial coordinates of the tissue detected, or of the density of intervening tissue. Further, Grass does not make use of the display of gamma-ray or x-ray peaks stripped of the display of radiation from Compton-scattered photons.

U.S. Pat. No. 5,068,883 (DeHaan) describes a contraband detection system employing two different sources of low-energy gamma rays, and a means of detecting backscatter from inspected objects. Depending upon the composition of the target volume, a portion of the gamma rays are backscattered and returned to the hand-held device. By quantitatively sensing these backscattered gamma rays, a rough qualitative determination can be made as to the density composition of the target volume. From such density information, reasonable inferences may be drawn as to whether the target volume includes certain types of contraband material. This patent does not disclose the combined use of both characteristic x rays and gamma rays in the determination of spatial coordinates of the material detected. Further, DeHaan does not make use of the display of gamma-ray or x-ray peaks stripped of the display of radiation from Compton-scattered photons.

Therefore, for the foregoing reasons, the prior art methods and devices used in nuclear medicine suffer from one or several drawbacks. Further, many of the prior art methods and devices relating to the use of radioactive isotopes do not disclose the use of both characteristic x rays and gamma rays, separately and/or simultaneously, in the determination of spatial coordinates of the tissue detected, or of the density of intervening tissue. Nor do they make use of the display of gamma-ray or x-ray peaks stripped of the display of radiation from Compton-scattered photons. None of the aforementioned prior art relates to the distribution of radiopharmaceuticals to the proximate guidance of external beam radiation therapy.

In copending U.S. patent application, Ser. No. 08/430,589, filed on Apr. 28, 1995, now U.S. Pat. No. 5,694,933 entitled Apparatus And Methods For Determining Spatial Coordinates Of Radiolabelled Tissue Using Gamma-Rays And Associated Characteristic X-rays, of which I am a co-inventor, which is assigned to the same assignee as this invention, and whose disclosure is incorporated by reference herein, there is disclosed apparatus and methods for localizing radiolabelled material, such as suspected cancerous tissue, which overcomes many of the disadvantages of the prior art. That apparatus and methods entail providing the tumor with a radioactive imaging agent, e.g., a radiotracer. As is known to those skilled in the art, ionizing radiation is named gamma radiation if the origin is from within the radioactive nucleus, characteristic x-radiation if the origin is from orbital electron energy transitions, and annihilation radiation if the origin is from interaction of a positively charged electron with a negatively charged electron, whereupon mass is converted into energy in the form of 511 keV photons. In all cases the ionizing radiation exists in known abundance. Both annihilation radiation and gamma radiation are commonly accompanied by characteristic x-rays. The apparatus and methods of the copending application and of this invention utilize a detector to detect the gamma rays or annihilation radiation and associated characteristic x-rays to faciliate the precise location of the tumor so that it can be removed surgically. In Particular, the disclosed embodiment of the system includes a radiation receiving device, e.g., a hand-held probe or camera, an associated signal processor, and an analyzer. The radiation receiving device is arranged to be located, e.g., hand-held, adjacent the body and the tumor for receiving gamma rays and characteristic x rays emitted from the tumor and for providing a processed electrical signal representative thereof. The processed electrical signal includes a first portion representing the characteristic x rays received and a second portion representing the gamma rays an annihilation radiation received. In a preferred embodiment of the invention the signal processor removes the signal corresponding to the Compton-scattered photons from the electrical signal in the region of the full-energy gamma ray and the characteristic x ray. The analyzer is arranged to selectively use the x-ray portion of the processed signal to provide near-field information about the tumor, to selectively use both the x-ray and the gamma-ray portions of the processed signal to provide near-field and far-field information about the tumor, and to selectively use the gamma-ray portion of the processed signal to provide extended field information about the tumor. This information can be used to provide the surgeon with a virtual map of the three dimensional distribution of suspected tumor tissue relative to the probe's position and angular orientation to precisely locate the tumor so that it can be sampled, and resected, if necessary.

The apparatus and methods of my aforementioned copending patent application Ser. No. 08/430,589 can be utilized with one or more radiopharmaceuticals for effecting the proximate guidance of external beam radiation therapy to cancerous or other tumor bearing tissue, e.g., tumor bearing lymph nodes, in accordance with the subject invention.

Heretofore the guidance of therapy radiation to suspected tumor tissue has been accomplished using various imaging techniques, e.g., CT scan, MRI, flouroscopy, etc., to provide the radiologist with a map or picture of the patient's anatomy. With this anatomical information the radiologist designs a plan to control the operation of an external radiation therapy machine, e.g., a linear accelerator, a X-ray machine, etc., to direct the desired radiation to the suspected tumor tissue. That plan may entail providing the radiation via plural portals into the suspected tumor site, since many tumors are so sized, shaped, or disposed with respect to normal organs, that they cannot be effectively irradiated from a single portal. Moreover, the amount and type of radiation provided may be different for one or more selected portals. While this technique is somewhat suitable for its intended purposes, it leaves much to be desired from standpoint of effectiveness in bringing a tumoricidal dose of external radiation to bear on the living tumor tissue, without causing damage to adjacent normal tissue.

One multi-portal radiation technique which has been utilized in some particular applications, e.g., irradiation of brain tumors, is the so called "Gamma-Knife" technique developed by Dr. Leksell. This technique entails localizing the suspected tumor using conventional CT or MRI imaging, followed by bombarding the suspected tumor site with external radiation from very large number, e.g., 201, of hemispherical directions to cause the radiation to intersect at a point where the suspected tumor is located. By so doing the cumulative radiation received by the tumor at the intersection point can be sufficiently high to kill the living cancerous cells, while the radiation applied to adjacent tissue is kept sufficiently low to prevent collateral damage to it. While this "Gamma-Knife" technique constitutes an improvement over other prior art techniques for applying external radiation to tumor tissue, it still leaves much to be desired from the standpoint of effectiveness and wide applicability. These limitations are particularly true for applications involving repeat or follow-up radiation treatment. In such a case the follow-up radiation provided by the Gamma-Knife technique may be delivered to already dead tumor tissue, i.e., tissue which had become necrotic, due to the previous or initial dose of radiation. As is known tumors have non-homogeneous response even to uniform radiation therapy, with some portions of the tumor becoming necrotic or fibrotic while other portions of the tumor continue to grow. External morphological imaging procedures are grossly inaccurate in determining the margins of surviving tissue. Accordingly, using the Gamma-Knife technique for follow-up treatment may result in damage to adjacent normal or bystander tissue without any significant concomitant tumoricidal benefit.

All of the above described drawbacks of prior art techniques for effectively irradiating internally located tumor tissue appear to be the result of the fact that the localization of the tumor is accomplished by merely examining the patient's anatomy while virtually ignoring the specific radiation attenuation characteristics of the path in the patient's body to the tumor site through which the therapy radiation will be applied. In contradistinction, the subject invention takes advantage of the body's own attenuation to serve as a guide for the application of external radiation to living tumor tissue. By so doing tumoricidal doses of radiation can be brought to bear on living tumor tissue, with little or no damage to normal bystander tissue. In particular, with the subject invention, the administration of one or more radiopharmaceuticals that go to the viable, growing remaining portions of tumor, e.g., metabolic or tumor localizing radiopharmaceuticals, allow specific increase in therapy to those specific small volumes where the therapy is needed, while sparing the adjacent tissue which will not benefit from additional radiation but which would, in all likelihood, have a high risk of adverse radiation overexposure related complications.

A number of radiotracers can be considered metabolic agents. Fluorine 18 deoxyglucose resembles glucose, the main cellular energy metabolism substrate. Deoxyglucose is taken up by cells which are in need of glucose. Once the deoxyglucose is inside the cell, it cannot be further metabolized. Thus, it stays in the location where it has been trapped and is not further degraded. Other radiotracers, like Thallium 201, resemble potassium which is transported into the cells when glucose is metabolized. $99^m$ Technetium Sestamibi is a radiotracer which localizes in proportion to the number and activity of mitochondrial, the principal metabolic energy factory within the cells. Thus, F18 deoxyglucose, Thallium 201, and $99^m$ Technetium Sestamibi can all be considered metabolic agents.

A general condition for the presence of any radiotracer within any tissue in the body is given by the reality that there must be blood flow to that tissue and there must be some extraction of that agent from the blood going through the tissue. Thus, blood flow times the radiotracer extraction rate serves to mark tissues that are still alive. Accordingly, other tumor localizing radiotracers including Gallium 67, as well as radiolabled peptides, antibodies, and fragments of antibodies may all serve to demonstrate areas of tumor which are alive, in contradistinction to areas of tumor that have died either because of previous radiation therapy, or because portions of the tumor have outgrown its blood supply, or because of other previous therapeutic interventions.

Thus, the subject invention has great utility in follow-up radiation treatment applications as well as in initial or primary radiation treatment applications.

OBJECTS OF THE INVENTION

Accordingly, it is a general object of this invention to provide apparatus and methods for providing external therapy radiation to living radiolabelled tumor tissue in the body of a living being which overcomes the disadvantages of the prior art.

It is a further object of this invention to provide apparatus and methods for providing a very accurate estimation of the depth of radiolabelled tissues beneath the overlying external skin tissue plane and thereby greatly mitigate the localization problems caused by background radiation in order to provide effective external therapy radiation to such radiolabelled tissues.

It is a further object of this invention to provide an apparatus and methods for providing external therapy radiation to living tumor tissue which has been tagged with a metabolic-indicating or other tumor localizing radiopharmaceutical.

It is a further object of this invention to provide apparatus and methods for localizing radiolabelled tissue, such as suspected living tumor tissue, within the body of a living being in order to apply effective external therapy radiation to such tissue.

It is a further object of this invention to provide apparatus and methods for localizing a radiolabelled tumor within the body of a living being in order to apply external therapy radiation to surviving portions of previously irradiated tissue.

It is a further object of this invention to provide apparatus and methods for localizing radiolabelled material, such as suspected cancerous tissue, within the body of a living being in order to apply external therapy radiation to such tissue to necrotize it, and if necessary to reapply external therapy radiation to surviving portions of previously irradiated cancerous tissue.

It is a further object of this invention to utilize characteristic x rays and full energy gamma rays in conjunction with apparatus and methods for localizing radiolabelled material, such as suspected cancerous tissue, within the body of a living being in order to apply and confine external therapy radiation to only living cancerous tissue.

It is a further object of this invention to provide apparatus and methods for detecting tumor localizing radiation emanating from living tumor tissue within the body of a living being to which a radiopharmaceutical has attached for precisely directing a beam of therapy radiation to that tumor tissue to necrotize it with minimal damage to adjacent viable, non-cancerous tissue.

It is a further object of this invention to provide apparatus and methods for utilizing characteristic x rays and full energy gamma rays to guide tumor targeting of external beam radiation therapy.

It is a further object of this invention to provide apparatus and methods for utilizing characteristic x rays and full energy gamma rays emanating from radiopharmaceutically tagged tissue to guide external beam radiation therapy.

It is a further object of this invention to provide apparatus and methods for utilizing characteristic x rays and full energy gamma rays emanating from radiopharmaceutically tagged internal tissue to direct electron beans or other high linear energy transfer means, such as heavy ion beams, and/or low energy x rays toward those areas where minimum overlying normal tissue separates the radiopharmaceutically tagged tissue from the skin.

It is a further object of this invention to provide apparatus and methods for utilizing characteristic x rays and full energy gamma rays emanating from radiopharmaceutically tagged internal tissue to direct the minimum essential megavoltage x ray beams or other uniform dose depth distribution beams toward those areas where thick overlying normal tissue separates the radiopharmaceutically tagged tissue from the skin.

It is a further object of this invention to provide apparatus and methods for directing the intensity and/or the type of radiation therapy beams to tissue tagged with a radiopharmaceutical for the purpose of minimizing the dose of such radiation to important organs.

It is a further object of this invention to provide apparatus and methods for directing the intensity and/or the type of radiation therapy beams to tissue tagged with a radiopharmaceutical for the purpose of maximizing the dose of such radiation to radiation resistant areas of the tagged tissue.

It is a further object of this invention to provide apparatus and methods for directing the intensity and/or the type of radiation therapy beams to tissue tagged with a metabolic or other tumor localizing radiopharmaceutical for the purpose of maximizing the dose of such radiation to surviving portions of previously irradiated tagged tissue.

It is a further object of this invention to provide apparatus and methods for effecting interactive real-time or almost real-time control of a machine to apply external radiation therapy to living tumor tissue localized by the detection of radiation emanating from a radiopharmaceutical localized to such tissue.

SUMMARY OF THE INVENTION

These and other objects of this invention are achieved by providing a system and methods for providing precise therapy radiation to living tumor tissue within the body of a living being. The system utilizes a tumor localizing radiopharmaceutical, e.g., a metabolic or other tumor localizing radiopharmaceutical, and basically comprises a controllable source of beam radiation and radiation detection means. The tumor localizing radiopharmaceutical is arranged for provision into the body of the being for attachment to the living tumor tissue therein, whereupon said radiopharmaceutical produces tumor-localizing radiation from that tissue, e.g., positrons or characteristic x rays and gamma rays.

In accordance with one preferred aspect of this invention the radiation detecting means is arranged to be brought into various positions adjacent the body of the being for detecting the tumor localizing radiation from a plurality of directions to provide an indication of the three dimensional distribution of the living tumor tissue to which the radiopharmaceutical has attached and for providing a signal indicative thereof.

The controllable source of therapy radiation is arranged for receipt of the signal, e.g., either directly or indirectly, to precisely direct a beam of the therapy radiation to the living tumor tissue to which the radiopharmaceutical has attached, to necrotize that tissue, with minimal damage to adjacent viable tissue.

DESCRIPTION OF THE DRAWINGS

Other objects and many attendant features of this invention will become readily appreciated as the same becomes better understood by reference to the following detailed description when considered in connection with the accompanying drawings wherein:

FIG. 1B is a diagrammatic side elevational view of a one embodiment of radiation therapy system utilizing the radiation detector and analyzer system shown in FIG. 1A in combination with a radiation therapy machine to effect the control of therapy radiation provided by the system;

FIG. 1C is an enlarged view taken along line 1C—1C of FIG. 1B;

FIG. 1D is a diagrammatic side elevational view, similar to FIG. 1B, but showing another embodiment of radiation therapy system constructed in accordance with this invention to effect the control of therapy radiation provided by the system;

FIG. 2 is a block diagram showing the components making up the system of FIG. 1A;

FIG. 3A is an illustration of a portion of the system shown in FIGS. 1A and 2 being used to determine the location of a radiolabelled tumor in the near-field in accordance with one aspect of the method of this invention, and in particular shows the approximate numbers of characteristic x rays and full energy gamma rays associated with the detection of 8000 disintegrations of Tc99m;

FIG. 3B is an illustration of a portion of the system shown in FIGS. 1A and 2 being used to determine the location of a radiolabelled tumor in the near-field in accordance with one aspect of the method of this invention, and in particular shows the approximate numbers of characteristic x rays and full energy gamma rays associated with the detection of 8000 disintegrations of In 111;

FIG. 4 is an illustration, like that of FIG. 3, but showing a portion of the system of FIGS. 1A and 2 at an initial step of being used to determine the location of a radiolabelled tumor located substantially in front of a kidney in accordance with one aspect of the method of this invention;

FIG. 5 is an illustration, like that of FIG. 4, but showing the system of FIGS. 1A and 2 being used in a later step in determining the location of the radiolabelled tumor of FIG. 4;

FIG. 9 is an illustration, like that of FIG. 8, but showing the system of FIG. 1A and 2 being used in yet a later step of determining the location of the radiolabelled tumor of FIG. 7;

DETAILED DESCRIPTION OF THE PREFERRED EMBODIMENTS

Figure 1A:
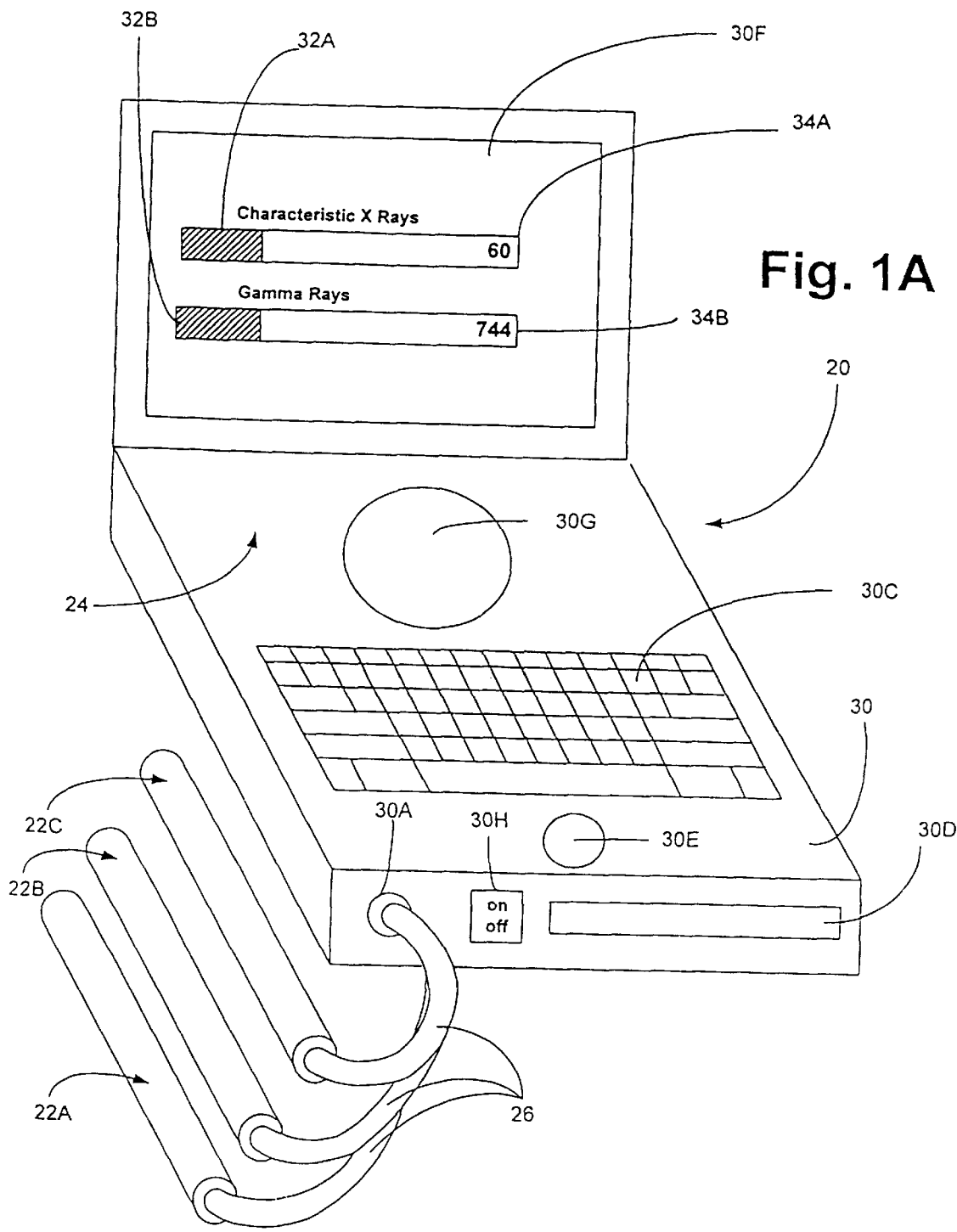
FIG. 1A is an isometric view of a radiation detector and analyzer system forming a portion of the radiation therapy system of subject invention.

Referring now to various figures of the drawing wherein like reference numerals refer to like parts in FIG. 1A there is shown a tumor localizing system 20 which together with a radiation therapy apparatus or machine 10 forms a radiation therapy system of subject invention. Two exemplary embodiments of the radiation therapy system are shown in FIGS. 1B and 1D.

The tumor localizing system 20 is constructed in a similar manner to that described in my aforementioned copending patent application. To that end, the localizing system 20 is arranged to determine the nuclear uptake of tissue, e.g., a tumor, lesion, or lymph node, which has been labelled or tagged with a radiopharmaceutical and to provide information to the radiation therapy practitioner or user regarding the location of the tumor with respect to some predetermined reference point. In accordance with a preferred embodiment of this invention the radiopharmaceutical utilized includes a metabolic agent or other tumor localizing agent so that it tags or attaches itself to living tumor tissue. One such metabolic radiopharmaceutical is Fluorine 18 deoxyglucose. Other metabolically indicative radiopharmaceuticals can be used, such as Technetium 99m Sestamibi, Thallium 201, Gallium 67, as well as peptides, antibodies and fragments of antibodies labelled with indium 111 or Technetium 99m or other radiolabels.

As will be described in detail later, the system of this invention makes use of the emitted gamma and characteristic x ray radiation from the radiopharmaceutically tagged tumor to measure the normal body tissue thickness that an externally emitted beam will encounter en route to the tumor. To achieve that end the tumor localizing system 20 includes at least one radiation detecting means, e.g., a probe 22, for detecting the radiation emanating from the radiolabelled tissue, and an associated analyzer 24. The analyzer 24 is arranged for analyzing the radiation detected by the detecting means to provide the radiation therapy practitioner with information to determine the center of the closest surface of the tumor, e.g., its "x" and "y" coordinates, as well as the distance or depth of that surface, e.g., the "z" coordinate, with respect to a predetermined reference point, e.g., the location of the probe. Thus, the system 20 serves to "localize" the radioactively tagged tissue. In addition the system 20 provides the practitioner with information regarding the density and/or amount of the intervening tissue lying between the tagged tissue and the predetermined reference point, and the amount of radiation attenuation provided by such intervening tissue.

In accordance with one aspect of this invention the system 20 provides signals indicative of the three dimensional distribution of the living tumor tissue to which the radiopharmaceutical has attached for the tumor targeting guidance of external beam radiation therapy. These tumor localization signals can be used to directly control a radiation therapy machine 10 or can be used as data by the radiation therapy practitioner to design a plan for irradiating the patient, i.e., indirectly controlling the radiation therapy machine. For example, as will be described in detail later, the tumor localizing system can be mounted on or made part of the machine 10, with the plural probes mounted on the machine's head so that their combined solid angle of acceptance is essentially coextensive and collinear with the therapy radiation beam which is projected from the machine's head. The machine includes computer control so that it can be made to traverse the area outside the patient's body in a cylindrical, hemispherical or fully spherical or other volumetric configuration while recording the intensity of activity received by the probes.

The intensity of radiation received from the probe can be used to modulate the intensity, energy, or type of radiation emitted from the radiation therapy port of the machine thereafter. Thus, if the radiation detected by the probe is quite high, indicating that the full thickness of the tumor is being sampled by the radiation detection probes, or that the tumor is particularly close to the surface in that spatial orientation, then the machine can be programmed to give a larger dose at that location in order to provide optimal deposition of radiation into the tumor with minimal deposition of radiation into overlying and underlying normal organs. By measuring the characteristic x-rays from the internally administered tracer, guidance for electron beam therapy and kilovolt x ray beam therapy can be provided. The concept is that the gamma and x-ray emissions of internally-administered radiation allow sensitive and specific guidance to the subsequent or coincident therapeutic emissions of radiation therapy beams. Moreover, the movement of the probes about the suspected tumor site to detect radiation from the radiopharmaceutical tagged tissue effectively provides the practitioner with a three-dimensional volumetric map of that tumor.

Heretofore, a three dimensional volumetric map of the tumor has been normally accomplished with single photon emission computed tomography using Anger gamma cameras. The subject invention entails a much simpler approach using one or several external probes which are provided with appropriate single hole or multiple hole collimation to map out the optimal boundary locations and to measure body attenuation of isotopes. These attenuation measurements can be used to modulate the external beam produced by the machine 10. For example, the machine's computer can be used to calculate the dose uniformity and dose distribution throughout the tumor tissue that can be achieved with minimum possible dose to bystander tissues, based on the acquired radiation emanating from the tagged tissue. Then the machine can be operated to provide the required electron beam and kilovoltage therapy at minimum possible dose to bystander tissues. Thereafter an additional iteration of the computation can serve to demonstrate what additional Megavoltage doses from which angles can complete the equalization of the uniformity of radiation deposited in the tumor at the least cost to biologically vulnerable bystander tissues. Thus, a relatively sophisticated way for optimization of the tumor targeted delivery of external beams of electron beam, kilovoltage, and megavoltage radiation therapy as well as heavy ion beam therapy can be achieved with the subject invention.

Where characteristic x-rays from the radiopharmaceutical in the tumor are detected, electron beams or kilovoltage x rays may be added to the therapy. Where the 140 keV gamma of technetium 99m are abundantly detected, additional kilovoltage therapy can be added. Where little gamma or x ray signal is detected, Megavoltage x-ray therapy beams are more appropriate.

In attempting to provide equivalent dose to the tumor from all orientations in applications with relatively high radiation attenuation, significantly more rays would be emitted in order to compensate for the attenuation in that particular line of orientation. A potential difficulty with such an approach, is that relatively high doses to bystander tissues are created in the process of equalizing the geometric distribution of dose within the tumor from multiple angular orientations. A hybrid situation may be preferable in which the map of gamma and characteristic x-ray emissions is used to do an initial calculation of distribution of dose throughout the tumor optimized for maximum dose being given along planes and orientations with minimal attenuation to maximally spare normal tissues. Selection of beam energies to spare normal tissues deep to the tumor is optimized by demonstration of three dimensional anatomy of tumor and normal tissues.

In the embodiment shown in FIG. 1B the external radiation therapy is provided by a machine 10 using the tumor localization and tissue attenuation signals produced by the system 20. To that end, the machine 10 constitutes a controllable source of therapy radiation arranged for providing at least one gamma or x ray or particulate therapy beam. In the embodiment shown in FIG. 1B the system 20 is coupled to the machine 10 so that electrical signals produced by the analyzer 24 are used directly by the machine 10 to automatically precisely direct the therapy beam to the tagged tissue, e.g., a tumor, to necrotize that tissue.

It should be pointed out at this juncture that the machine 10 may be a conventional radiation therapy machine, e.g., an x ray machine or a linear accelerator for producing a low energy electron beam, a high energy electron beam, or a beam of heavy ions, or beams of kilovoltage or megavoltage x rays or gamma rays, etc. The therapy machine sold by Varian Associates under the registered trademark CLINAC 2300C/D appears to be quite useful for implementing this invention since it lends itself to modulation of electron and megavoltage x-ray beams, as may be required for a specific therapy application. Other conventional therapy machines can also be utilized. Alternatively, the machine 10 may be a specially constructed one.

In the case where the radiation therapy machine 10 is conventional, in accordance with one preferred embodiment of the invention at least one (and preferably, three) detecting probes 22 are mounted by any suitable means, e.g., a bracket (not shown), on the head of the machine 10 while the remainder of the localization system 20 (i.e., the analyzer 24) can be disposed adjacent the machine or built into it (e.g., located within the machine's console). The probes 22 are preferably located at equidistantly spaced locations about and close to the port from which the therapy beam is projected. The probes are arranged to receive radiation from a radioactively tagged tumor located within a field defined by the solid angle of the beam of therapy radiation produced by the machine 10. To that end the probes are oriented so that they are aimed in the same direction and their combined solid angle of acceptance is essentially coextensive and colinear with the therapy radiation beam, which can be narrow or broad. Accordingly, when the head of the machine is oriented so that the probes pick up the radiation emanating from the radiolabelled tissue, i.e., the living cancerous tissue, that tissue will be within the field of the therapy radiation beam produced by the machine.

It should be pointed out at this juncture that the radiation detector(s), e.g., probes(s) of the tumor localizing system 20 can be built into the radiation therapy machine 10 instead of being mounted thereon.

Alternatively, the radiation localization portion 20 of the radiation therapy system of this invention can make use of a single gamma camera, e.g., an Anger camera or preferably a solid state gamma camera (possibly using CdZnTe detectors), in lieu of the one or more probes 22. In such an alternative arrangement the gamma camera is preferably located opposite to the head of the machine 10 and coaxial with the exiting therapy beam so the field of view of that camera is essentially coextensive and collinear with the therapy radiation beam, as shown in FIG. 1D. Such a configuration allows transmission imaging of the patient with suitable x rays of diagnostic energy and intensity produced by the therapy machine. The detector 100 of this invention could easily be used for fluroscopy, CT scanning, and gamma ray imaging. Moreover, isotope detection and computed tomography can be accomplished simultaneously in accordance with this invention by acquiring the gamma ray full energy peak and the CT x ray peak of a different, and lower energy. For example a Technetium radiolabelled pharmaceutical may be acquired at 130 to 150 keV, while the CT images is acquired at an energy of 40 to 50 keV at perhaps 20 times higher photon flux. Thus, one can achieve absolute coregistration of CT images and nuclear information for optimal therapy beam guidance.

In accordance with one aspect of this invention the radiation localizing signals produced by the analyzer 24 of the tumor localizing system 20 can be provided directly to the radiation machine's controller, e.g., its microprocessor (not shown), so that the controller precisely controls the machine's operation, whereupon the optimum type and energy of the therapy radiation beam is automatically directed to the tagged tissue, and nowhere else. For example, in response to receipt of the tissue localizing signals from the analyzer 24 the machine's microprocessor can be arranged to cause the head of the machine 10 to be moved about the patient to apply a specific type or types radiation at a specific energy level from various angles and directions, i.e., portals, to ensure that only the living tumor tissue, i.e., the tissue to which the radiopharmaceutical has attached, is irradiated. This action prevents injury to adjacent viable normal or bystander tissue, while necrotizing the cancerous tissue of the tumor.

It should be noted that the subject invention also may be used to effect the non-automatic control of a radiation therapy apparatus 10. In this regard, the radiation localizing signals produced by the analyzer 24 of the tumor localizing system 20 are not directly used by the machine 20 to control its operation. Instead the radiation localizing data of the signals provided by the analyzer 24 can be used by the radiation therapy practitioner to provide a map from which a radiation therapy plan can be developed. Similarly, a transmission map obtained by using diagnostic energy and intensity x rays produced by the therapy machine and detected by the gamma camera can be used to guide therapy. Once the plan is established it can be implemented at any time by dialing or keying in the control parameters into the machine 10 to control its operation.

The living tumor tissue localization action of the localizing system 20 is accomplished by making use of the following behavior of photons as they travel through a substance, such as human tissue: the higher the energy of a photon, the further that photon is likely to travel through tissue of a given density and atomic number before it is scattered or absorbed; the greater the density and the greater the atomic number of the substance, the shorter the distance that a photon of a given energy is likely to travel before being scattered or absorbed; and in the instance of x rays and gamma rays, the greater the density and the greater the atomic number of the substance or the further the distance that the corresponding x rays or gamma rays travel, the greater the probability that the corresponding peak line shape will be asymmetrical. These behaviors depend upon the energy of the photon involved, not whether that photon is an x-ray photon or a gamma-ray photon.

Decisions made by the practitioner using the radiation detecting means regarding the presence or absence of clinically meaningful nuclear uptake in tissue must be based upon statistically significant data. The number of photons detected from sites of clinically meaningful uptake must be sufficiently abundant, relative to sites without meaningful uptake, such that the comparison of said numbers allows for sound statistical treatment which will provide the appropriate level of confidence to the practitioners. Accordingly, the time periods used for measurements of detected photons, and the amounts of radiotracer injected into the patient must be such to allow for sufficiently abundant photons to be emitted and detected from said sites of meaningful uptake, for the disease state or states of interest.

As will be appreciated by those skilled in the art from the discussion to follow, technological advancements that enable the subject invention to substantially overcome the previously mentioned drawbacks associated with prior art radiation imaging techniques have now been developed. For example, improved tumor detection can be achieved by placing a nuclear uptake probe or detector adjacent the body during radiation therapy, with or without having surgically exposed the tissues of interest thereby reducing the thickness of intervening tissues, in order to detect and evaluate radioactive emissions including gamma-ray photons and characteristic x-ray photons for guidance of intraoperative radiation therapy. Moreover, nuclear uptake probe systems that allow the practitioner to electronically select and view only photons within a specific range of energies are available. In addition, multi-channel analyzers have long been available to display meaningful peaks, corresponding to gamma ray and characteristic x-ray photon counts, arising from the continuum produced by Compton-scattered photons. All of the foregoing have contributed to the making of the subject invention, whose basis is the utilization of the characteristic x rays together with the "full-energy" or "primary" gamma rays of the radiolabeled tracer such that the number of detected x rays and the number of detected gamma rays can be used separately, and can be compared, to provide information to the practitioner regarding the location of tissue with nuclear uptake, including information on the depth of said tissue beneath the exposed or exterior tissue plane, and also information on the density of intervening tissue. The characteristic x rays have heretofore been usually undetected, or, if detected have usually been ignored due to the fact that they are of low energies and sometimes of low abundance so that when commingled with the relatively intense Compton-scattered photons, their signals are very difficult to extract.

By utilizing an optional aspect of this invention, the counts or events associated with detected Compton-scattered photons can be stripped away and eliminated by numerical fitting techniques, leaving only the characteristic x-ray and the full-energy gamma-ray peaks(s) for evaluation. As will be discussed later, software is commercially available to facilitate this process. Alternatively, or in addition, collimation can be utilized for restriction of field of view to reduce signals from unwanted Compton-scattered photons and other extended field background radiation.

Before describing the tumor localizing system 20, a brief description of the manner in which the tumor will have been tagged with a radiolabelled tracer will now be given. In particular, the patient is injected with a selected radiotracer 8, which may be Fluorine 18 deoxyglucose, monoclonal antibodies or other disease specific or anatomically or physiologically specific agents, labeled with one or more radioisotopes. Sufficient time is allowed for the radiotracer to circulate throughout the body and adhere to or be absorbed at the particular site-of-interest, e.g., cancerous tissue cells or tumors. As previously stated, often only a small percentage, e.g., one-half to five percent, of the radiotracer will actually be absorbed by or adhere to the organ or tissue that is of clinical interest and intended for examination, i.e., the site of "specific uptake". A much larger portion of the injected radiotracer often circulates to other areas of the body and interacts with body tissue and organs that may not be of clinical interest, such as non-cancerous tissue, circulating blood, bone marrow, extracellular fluid, the liver, and kidneys. Therefore, after circulating through the patient's body over a period of time, the radiotracer will concentrate at sites of specific uptake and will reside in dilute to high concentrations in some non-cancerous tissues, organs, extra-cellular fluid, and blood. High to very high concentrations of such "non-specific" uptake may be found, for example, in liver, with many Indium-111 labeled antibodies, and in kidneys with many Technetium-99m labeled antibodies, as discussed earlier.

A radioisotope that is highly suitable as a radiolabel, to be part of a radiotracer to be injected into the human body in accordance with this invention, is Technetium 99m with the metabolic agent Sestamibi. This radiotracer emits full-energy gamma rays of 140 keV and characteristic x rays of approximately 19 keV. Indium 111 octreotide is an example of an additional radiotracer that may be employed in accordance with this invention. Indium 111 emits full-energy gamma rays of approximately 247 keV and 172 keV and characteristic x rays of approximately 24 keV. Iodine 123 can also be used. This isotope emits full-energy gamma rays of approximately 159 keV and Tellurium characteristic x rays of approximately 27 keV may also be used. Iodine 125 which emits full-energy gamma rays of 35 keV and Tellurium characteristic x rays of 27 keV may also be used, generally for tissues at depths not exceeding three centimeters. Other radioisotopes which may be used are Gallium 67, as well as all nuclear medicine imaging isotopes and positron emitting isotopes. These positron emitting isotopes are preferrably combined with a metabolic agent, e.g., deoxyglucose to form F18 deoxyglucose, to ensure their uptake or adherence to living tumor tissue. Since dead tissue has very low blood flow and extraction rate, other tumor localizing radiotracers are also useful.

Tumor localizing radiotracers including metabolic tracers generally accumulate in some normal tissues as well as in tumor. Accordingly, the radiation therapy practitioner designates the areas of the image in the following categories: (A) tumor, (B) normal radiation resistant tissue, (C) normal radiation sensitive tissue, and (D) critical radiation sensitive tissue. The tissue category (A) represents that volume of tumor that has adequate blood flow and adequate extraction rate of radiotracer to demonstrate continued presence of live tumor cells. The tissue category (B) includes muscle and most bone, with the exception of joints, especially the hip joint. The tissue category (C) includes areas of heavy bone marrow presence, such as the spine, most major skeletal joints, kidneys, spleen, and other major organs, including the liver. The tissue category (D) includes all areas that have been previously irradiated that contain vital body organs, such as the kidneys. The spinal cord or other portions of the central nervous system that have been previously irradiated are also considered critical sensitive tissues to the extent that they are close to the threshold for showing irreversible radiation-induced damage.

Radiation therapy dose planning maximizes one dose to tumor while progressively decreasing doses to tissue categories (B) and (C). In order to greatly decrease complications of therapy, radiation dose to category (D) tissue is reduced to the maximum extent compatible with achieving tumor control through heavily preferential use of radiation ports that do not irradiate critical tissue.

As can be seen in FIG. 1A this embodiment of the tumor localizing system 20 includes three identical, nuclear uptake probes 22 (or other radiation detectors). As mentioned earlier, the localizing system 20 may only include a single probe 22 (or other radiation detector). In any case, the system 20 includes an electronic instrument 24 for processing signals from the probe(s) 22. In accordance with one preferred embodiment of this invention, each probe is a small hand-held device, like that provided by Care Wise Medical Products Corporation of Morgan Hill, Calif., the assignee of this invention, under the trademark C-Trak®. The construction of each probe 22 can best be appreciated by reference to FIG. 2 where it can be seen the each probe basically comprises a body member 22B formed of a radiation blocking material and having a hollow interior in which a radiation detector, e.g., a scintillation crystal 22C and an associated photomultiplier 22D are located. The front end or nose 22A of the probe defines a window or opening through which photons are received to hit the scintillation crystal 22C. Typically, the scintillation crystal 22C is comprised of either Sodium Iodide doped with Thallium, or Cesium Iodide doped with Sodium or Thallium.

The probe 22, whether mounted on a radiation therapy machine or some other equipment or hand-held, is arranged to be oriented sot that it is coaxial to the radiation therapy beam and located closely adjacent the site of the suspected tumor. If desired, the probe may be inserted through a natural body orifice, through a surgical wound or percutaneous incision or puncture to facilitate its placement. When placed within the proximity of the suspected tumor, the probe detects photons emitted or scattered from tissue lying within the probe's "field-of-view" 12. This field-of-view, as represented by the phantom lines in FIGS. 3–11, is sometimes called the "solid angle of acceptance", and is established by the size, depth, shape and location of the probe's window or opening with respect to its crystal 22C, and the size and shape of the crystal. The field of view can be described as a volume, typically conical or cylindrical in general shape, extending indefinitely into the space that is "viewed" by the detector through its window.

In accordance with a preferred aspect of this invention the probe 22 includes a collimator 22E located at the probe's window to establish the probe's field of view. The collimator 22E may be fixed or variable, as desired. In either case the desired acceptance angle of the field-of-view can be established. This feature may expedite the tumor localization procedure, as will be described later.

The probe 22 includes a output cable 26 coupled to the output of the photomultiplier. The cable includes a connector at its end which is arranged to be connected to an input connector 30A of the instrument 24 to provide electrical signals in the form of charge pulses in response to the receipt of photons by the probe. In particular, as photons are received by the probe they hit the scintillation crystal 22C, which causes the crystal to give off flashes of light or "scintillations" whose intensity is proportional to the energy of the photons received. The light flashes are intercepted by the photo cathode forming the front of the photomultiplier wherein electrons are released to provide electrical pulses which are proportional to the energy of the photons detected, with the number of pulses being proportional to the number of photons received. The resulting electrical signal is provided by the cable 26 to preamplifier and associated amplifier circuitry 30B (FIG. 2) which will be described later. The circuitry 30B forms a part of the instrument 24, but may be a separate component interconnected between the output of the probe and the input of the instrument 24. It is in the instrument 24 that the signal representative of the radiation detected by the probe 22 is processed and utilized in accordance with the present invention.

In an alternative embodiment of this invention, the detector used in the probe 22 is of a high resolution semiconductor design capable of directly converting detected radiation into electrical signals. In examples of such alternative embodiments the detector may be comprised of Cadmium Zinc Telluride, Germanium, or Silicon. Arrays of such detector elements may constitute a solid state "gamma camera."

Another alternative embodiment of a probe for use in the system of this invention may have more than one detector, such as a probe with two independent detectors or independent segments of a detector, each of which is intended to monitor radiation from a specific kind or category of sites or of a specific energy or range of energies.

It should be pointed out that other radiation detecting means can be used with the system of this invention in lieu of the hand-held probe 22 described above. In this regard a conventional gamma camera, or some other detector or operative camera can be utilized to detect the radiation emanating from the material to be localized.

When the probe 22 is located at some operative position with respect to the patient's body, the probe will detect an immense amount of photon emissions within its field-of-view. This includes full-energy gamma-ray and characteristic x-ray photons and Compton-scattered photons. These photons can originate from areas of no clinical interest and from sites of specific uptake, which are of clinical interest.

The instrument 24 provides a means for separating and displaying information obtained from the detection of photons of any specific energy or range of energies from that obtained from the detection of the other photons within the field of view, and also for further evaluation of this information based on relationships between the numbers of photons of different energies, such as those of the characteristic x rays and the full-energy gamma rays of a specific radioisotope (or radioisotopes), and also for further evaluation based on the effects of the passage of such photons through tissue. In particular, as will be described in detail later, the system of this invention provides the radiation therapy practitioner with a means for selectively monitoring only those photons of interest in clinical evaluation and to estimate the depth of tissue from which these photons originate, in order to determine the lateral location, e.g., X and Y coordinates, and the distance or depth location, e.g., Z coordinate, of the site of specific uptake, i.e., the suspected tumor.

The instrument 24 includes means to be described later which is arranged to sort the amplified electrical signals representative of the photons received by the probe by energy. As can be seen clearly in FIGS. 1 and 2 the instrument 24 basically comprises a lap-top microcomputer 30 which has been modified to include a multichannel analyzer and associated components (all to be described hereinafter). In particular, the instrument 24 includes the heretofore identified input connector 30A, the heretofore identified preamplifier/amplifier circuitry 30B, a conventional keyboard 30C, a floppy disk drive 30D, a hard disk drive and/or Read-Only-Memory ("ROM") drive (not shown), a trackball 30E or other pointing device, a color or monochrome display panel 30F, a loudspeaker or other annunciator 30G, an ON/OFF switch 30H, and various software or programs, files, etc., which the lap top computer uses for performing the various functions of the subject invention. It should be pointed out that such software, programs, etc., can be replaced by hardware or firmware to achieve the same ends.

The probe 22 described earlier is preferably constructed so that it has sufficient energy resolution to discern the characteristic x-ray signals and full-energy gamma-ray signals despite the continuum arising from Compton-scattered photons in some clinical settings. Moreover, the use of a collimator should aid in discerning the desired gamma rays and characteristic x rays detected from the Compton continuum in such clinical settings, by allowing only those Compton-scattered photons which come from within the field of view set by the collimator, and which are of a direction that results in them reaching the detector, to be detected. However, in some applications further reduction of the effects of the Compton continuum is desired. For such settings, one preferred embodiment of this invention utilizes means to remove or strip away the data representing the continuum arising from Compton-scattered photons in the vicinity of the characteristic x-ray peak(s) and in the vicinity of the full-energy gamma-ray peak(s). The means for accomplishing that action is provided by curve fitting software which is well understood by users practiced in the art of nuclear instrumentation for medical and non-medical applications.

The multichannel analyzer forming a portion of the instrument 24 is designated by the reference number 30I and is of conventional construction. For example, the implementation of the multichannel analyzer in the instrument 24 can be effected by use of a plug-in printed circuit card assembly for a personal computer ("PC Card") or PCMCIA card. One such PC Card is the multichannel scaler card sold under the trade designation MCS-PLUS by EG&G Ortec of Oak Ridge, Tenn. Alternatively, the analyzer may be constructed like that sold by Aptec Nuclear, Inc. of North Tonawanda, N.Y. 14120-2060, under the trade designation ODYSSEY 4. In any case the analyzer (30I) preferably has at least 256 channels for sorting the input signals from the probe 22 according to the energy of the photons detected. To that end, each channel of the analyzer has an energy width (e.g. about one keV ) in order to provide suitable energy resolution of photons of various energies which are detected by the probe 22. The computer making up the instrument 24 is connected to the multichannel analyzer's output (not shown) to receive signals indicative of the energy of the photons picked up by the probe and is equipped with commercially available software, to be described later, resident on the hard disk or in ROM. This software, in combination with the hardware of the computer, establishes the following functional elements of the instrument 24: peak identification means 30J, window setting means 30K, characteristic x-ray isolation means 30L, full-energy gamma-ray isolation means 30M, ratio calculation means 30N, subtraction calculation means 30P, spectral line shape recognition means 30Q, characteristic x-ray and full-energy gamma-ray normalization means 30R, bar graph display and numeric display drive means 30S, and annunciator drive means 30T.

Before describing the details of the various means making up the instrument 24 a brief discussion of the mode of use of the system 20 is in order. In the interest of ease of understanding the following discussion will consider the use of a system 20 having only a single probe (e.g., a probe mounted on the head of a radiation therapy apparatus at the therapy port), it being understood that in a preferred embodiment of this invention the system 22 includes plural probes 22 mounted on the radiation therapy apparatus 10 (as described earlier). In such a case the plural, apparatus-mounted probes are moved in unison by moving the apparatus' head.

The radiation therapy practitioner orients the probe 22 to the desired position adjacent the suspected tumor site and uses the probe to detect emitted photons initially by very slowly moving the probe 22 over areas of interest, while listening to the audible signal produced by the annunciator 30E and/or while observing the bar graphs and photon counts provided on the visual display panel 30F. These bar graphs display the number of photons being detected, thus confirming appropriate probe orientation for guidance of radiation therapy.

As earlier, the time period for the measurements, and the amount of radiotracer injected into the patient must be such that the numbers of emitted photons detected and displayed, and the differences and/or ratios of said numbers of photons which are used to determine the presence or absence of specific uptake represent statistically significant differences that will provide the practitioner with a sufficient confidence level.

During this "sampling" period, the multichannel analyzer 30I receives signals from the preamplifier amplifier circuitry 30B. The peak voltage of each signal received during the sampling period corresponds to the energy of each photon detected by the probe 22. Specifically, the multichannel analyzer 30I stores in memory each signal it receives from the probe 22 during the sampling period and assigns each of those individual signals to a particular channel within it based on the signal's associated voltage. As additional photons are detected by the probe 22 they are distributed into the various energy channels in the multichannel analyzer. The multichannel analyzer generates an electrical output signal, which if plotted, constitutes a spectrum or histogram of the number of counts of photons detected as a function of their energies.

Figure 14:
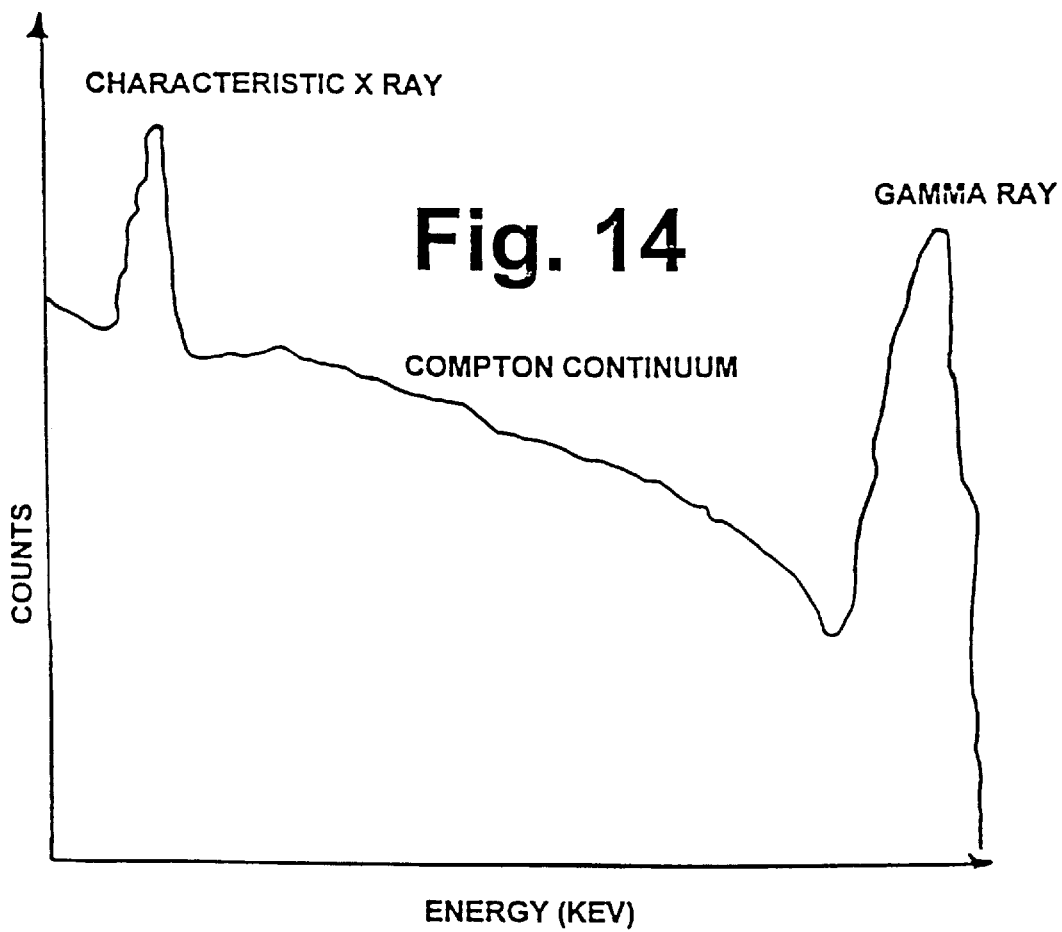
FIG. 14 is a histogram, like FIG. 12, but showing the spectrum of radiation counts obtained by the system of FIGS. 1A and 2 during the localization of the tumor in accordance with one aspect of this invention.

A typical spectrum plot for Technetium 99m is shown in FIG. 14. The spectrum plot represents graphically the accumulation of photons detected from Technetium 99m radio-labelled tissue by the probe 22 over a fixed time period, and is comprised of three components, i.e., at least one full-energy gamma-ray peak, at least one characteristic x-ray peak, and the continuum arising from Compton-scattered photons. The y-axis of the spectrum plot represents the number of events, i.e., the number of photons detected within a given time period at a given energy, while the x-axis represents the energy of detected photons. It should be understood that the spectrum plot illustrated in FIG. 14 is comprised of raw data. That is, the spectrum plot represents all photons detected by the probe 22 within its field-of-view, i.e., all detected characteristic x-ray photons, full-energy gamma-ray photons, and Compton-scattered photons. These include photons originating from sites of specific uptake that are of clinical interest, and may as well include photons originating from background, such as circulating blood and bone marrow.

The output of the multichannel analyzer or histogram is provided to the peak identification means 30J. This means is arranged to determine if the number of photons detected are above a baseline generally corresponding to the Compton continuum, in order to identify the characteristic x-ray and full-energy gamma-ray peaks. The peak identification means can be implemented by any suitable software resident in the computer 30.

The output of the peak identification means 30J is provided to the window setting means 30K. This means, which is also implemented by suitable software resident in the computer 30, establishes the upper and lower energy limits so as to establish the width of the energy band or window encompassing the characteristic x-ray peak and the energy band or window encompassing the full-energy gamma-ray peak.

The output of the window setting means is provided to the characteristic x-ray isolation means 30L and the full-energy gamma-ray isolation means 30M. These means, which will be described later, effectively strip or remove substantially all of the effects of Compton-scattering from the numbers of photons whose detection is displayed. While this function is of considerable importance in many applications, in others it is not. With regard to the latter, in order to determine the site(s) of specific uptake in accordance with this invention it is not necessary in some cases of clinical importance to first remove the continuum arising from Compton-scattered photons from the displayed data in the region of the characteristic x-ray and full-energy gamma-ray peaks. Melanomas of the hands and feet may also not require removal of the display of Compton continuum in order to identify characteristic x-rays.

However, in many instances it will be desirable to substantially strip the data representing the detection of the Compton-scattered photons away from the data at least in the region of the characteristic x-ray and full-energy gamma-ray photon emissions. Consequently, the preferred embodiment of this invention, shown herein, includes a Compton-stripping or neutralizing feature. This action is accomplished by the characteristic x-ray isolation means 30L and the full-energy gamma-ray isolation means 30M. Those means are comprised of computer software for performing mathematical curve fitting and stripping functions. In particular, the characteristic x-ray isolation means 30L and full-energy gamma-ray isolation means 30M when operating in the computer 30 serve to filter out the fraction of events that represent Compton-scattered photons, and pass through for display the data on characteristic x-ray photons and full-energy gamma-ray photons.

In accordance with a preferred embodiment of this invention the isolation of characteristic x-ray and full-energy gamma-ray photons by the means 30L and 30M can be accomplished by readily adapting existing commercial curve fitting and curve stripping mathematical software. Such modified software is resident in the computer 30 of the instrument 24, e.g., stored on the hard drive, on Read-Only-Memory, or on a card in the computer. Examples of usable or readily adaptable commercial software are the software sold under the trade designation PCA-II Second Generation Software by Oxford Instruments, Inc., Nuclear Measurements Group, of Oak Ridge, Tenn. 37831-2560, the software sold under the trade designation SIGMASTAT statistical software by Jandel Scientific Software of San Rafael, Calif. 94912-7005, and the software sold under the trade designation MATLAB and MATLAB Toolboxes by The Mathworks, Inc. of Natick, Mass. 01760-9889.

An alternative and simpler manner of substantially removing the data on detected Compton-scattered photons can be achieved by modifying the isolation means 30L and 30M to examine the data within a narrow energy range or "window" just above the highest energy displayed in the characteristic x-ray photopeak. In particular, the software of the instrument 24 can be arranged to examine the data on detected photons within a predetermined energy bandwidth, e.g., a 4 keV, "window" immediately above the energies of the characteristic x-ray peak. The data within that window can then be subtracted from the data on photons detected within a similar sized window encompassing the characteristic x-ray peak to provide a somewhat crude removal of Compton-scattered photons. A similar technique can be used to strip Compton-scattered photons from the vicinity of the trailing edge of the gamma-ray photopeak. If more precise stripping is required or desirable in the vicinity of the characteristic x-ray peak, the software can be arranged so that the data from a second predetermined width, e.g., 4 keV, window lying just below the energy displayed in the characteristic x-ray peak is examined. Then the mean of the numbers of photons detected in the window immediately above, and the window immediately below the energies of the x-ray peak is calculated and subtracted from the number of photons detected in the window making up the x-ray peak to result in a more precise stripping of the Compton-scatter.

Where higher resolution or precision is desirable, another approach is to use the isolation means 30L and 30M to mathematically fit a function using conventional curve fitting techniques to the portion of the histogram representing Compton-scattered photons and to subtract that function from the histogram of detected photons, thereby resulting in a substantially Compton-stripped signal or histogram representing primarily the characteristic x-ray photons and full-energy gamma-ray photons.

Figure 1E:
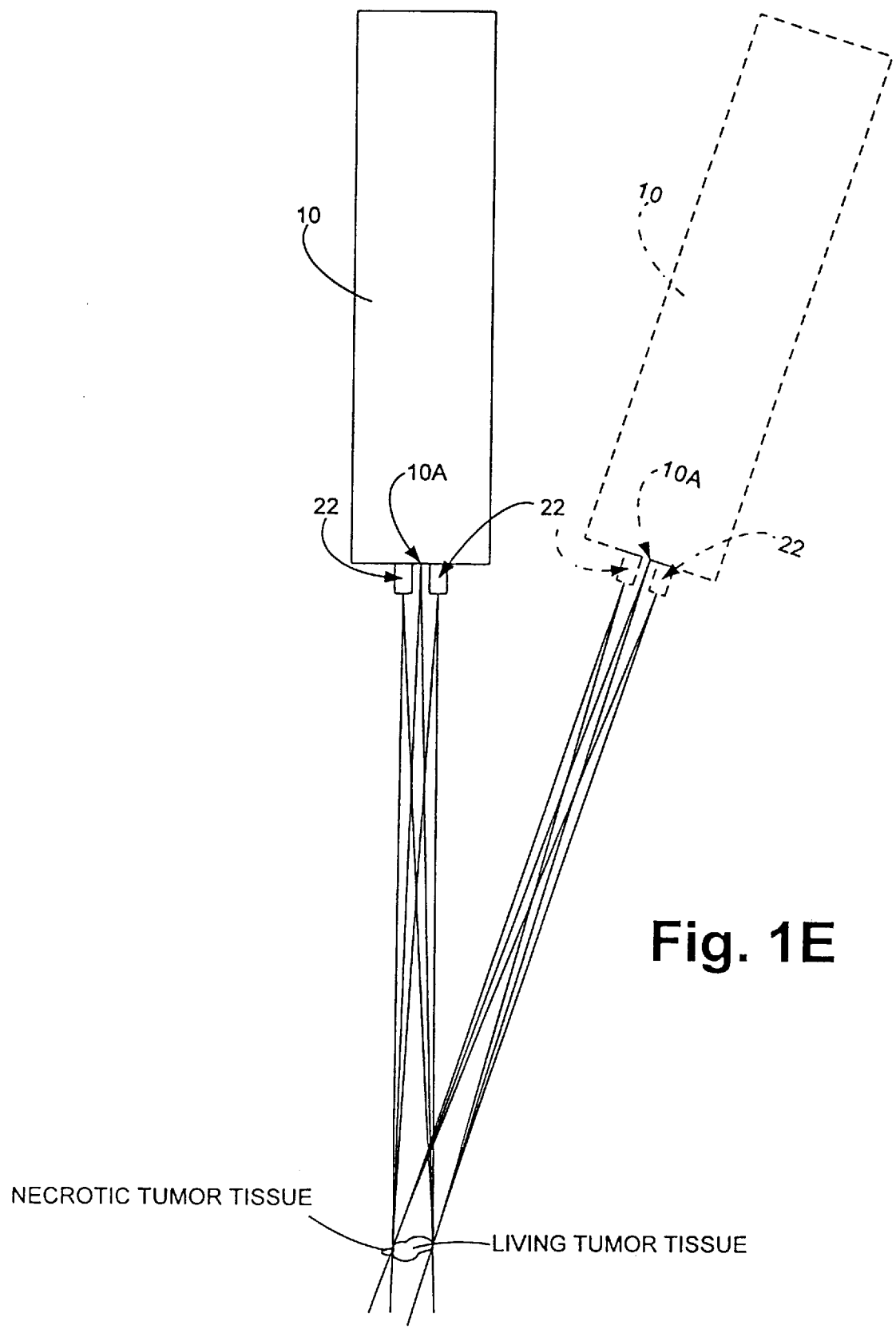
FIG. 1E is a view like that of FIG. 1B, but showing the application of therapy radiation to a tumor from multiple directions using the system.

With the Compton continuum substantially stripped away, the analyzer provides the line shape of each peak, and also a measure of the number of characteristic x-ray photons and full-energy gamma-ray photons detected within the sampling period. The instrument 24 presents this information to the practitioner in visual and audible form. In particular, the information is displayed visually in the form of two bar graphs depicting the numbers of the characteristic x rays and full-energy gamma rays detected within a given time period, and associated numeric displays of the same on the video screen 30F. This is shown clearly in FIGS. 1 and 9–11. As can be seen therein, a light bar or graph 32A whose length represents the number of characteristic x rays detected, and a light bar or graph 32B whose length represents the number of full-energy gamma-ray counts received are displayed on the video screen or panel 30F. In accordance with a preferred embodiment of this invention the bar graphs 32A and 32B are normalized to the naturally occurring abundance of characteristic x rays to full-energy gamma rays for the particular radioisotope used, so that when photons are detected in the correct ratio for the natural abundance of characteristic x rays and full-energy gamma rays for the particular radioisotope, the two bar graphs will be of the same length (as shown in FIG. 1). Associated with the bar graph 32A on the video screen 30F is a numeric display 34A representing the characteristic x-rays detected, while a similar numeric display 34B representing the number of full-energy gamma rays detected is associated with the bar graph 32B. The bar graphs 32A and 32B and the associated digital displays 34A and 34B, respectively, are produced under control of the bar graph and digital display driver 30S. This driver is implemented by any suitable software in the computer 30.

The information regarding the photons detected is provided audibly by the annunciator 30G, e.g., a speaker or tone or voice synthesizer, under the control of the annunciator driver 30T. The operation of these means will be described later.

The practitioner can utilize the information on the display screen 30F and the information provided by the annunciator 30G in ways to be discussed below, to determine the locations and to evaluate the depth of sites of specific uptake for the tumor targeting guidance of external beam radiation therapy.

In some preferred embodiments of this invention, as will be discussed later, a library of spectra of Technetium 99m, Indium 111, Iodine 123, Iodine 125, Iodine 131, Thallium 201, Gallium 67, Fluorine 18, and other such radionuclides of interest is assembled and resident, e.g., stored within the computer of the instrument 24. Available data, such as that provided by performing point source measurements of radiation passing through a water equivalent tissue material or water itself, from two millimeter increments of depth or "thickness" to water depths of 30 millimeters, and at five millimeter increments for depths from 30 to 200 millimeters is preferably obtained from empirical measurements or available data. In any case a library of data on the various radioisotopes is stored in the instrument 24 or on diskette for input into the instrument. This makes available to the system 20 a reference library of information on the effect of the thickness or depth of tissue through which emitted radiation passes on such factors as: attenuation of characteristic x rays and full-energy gamma rays; the line shape of the spectra of full-energy gamma-ray peaks and characteristic x-ray peaks; and the ratio of full-energy gamma rays to associated characteristic x rays. All of that data will be useful for localizing a site of specific uptake, e.g., a tumor, as will be described later.

The window setting means 30K assists in locating sites of specific uptake and obtaining other information regarding structures within the body by electronically selecting for evaluation a specific energy range of the immense amount of photon information within the probe's field of view. However, before describing the window setting means 30K the following discussion of the problems in discriminating sites of specific uptake is in order. To that end, and as will be appreciated by those skilled in the art, as the distance measured along the central longitudinal axis of the probe 22 from its window increases, the number of potential sites from which emitted photons can be detected increases. That is, with increasing distance a probe's field-of-view will typically contain an increasing amount of received emissions. By evaluating the entire field-of-view, it may be extremely difficult to determine the exact location of the site of specific uptake. For example, gamma-ray photons are capable of traveling relatively great distances, i.e., tens of centimeters, through soft tissue without being absorbed. Since it is possible for full-energy gamma-ray photons to originate from distant sites of specific uptake, as well as from distant sites of non-specific uptake, located deep within field-of-view, it is difficult to determine with a high degree of certainty the exact site from which such gamma-ray photons originate.

Conversely, characteristic x rays are typically comparatively low energy emissions that can travel only ten (10) to thirty (30) millimeters through soft tissue before being absorbed. For example, the half-value layer in water (i.e., the thickness which will absorb one-half of the incident x rays) for 20-keV x rays is about ten millimeters; for 30-keV x rays, 21 millimeters; and for 40-keV x rays, 28 millimeters. For point sources, the inverse square law also operates, further limiting depth of detectability. In addition to absorption, photons passing through tissue (or water) can also be Compton-scattered, but not absorbed. The photons arising from this scattering process have lower energies by virtue of having been scattered. Both absorption and Compton-scattering result in a reduction of the number of photons recorded in a given x-ray peak.

The energies of the characteristic x rays of Indium 111 are about 24 keV, and of Technetium 99m are about 19 keV; therefore very few are detectable beyond a tissue depth of 30 millimeters. Detected characteristic x-ray photons from these radioisotopes will therefore originate from tissue lying at shallow depths within the field of view, such that the location of the site of their origin will be within a much smaller and better-defined volume of tissue than would be the case for tissue located by the detection of higher energy gamma-rays alone.

The subject invention enables the practitioner to examine the characteristic x-ray photons received by the probe to determine that the site of specific uptake, e.g., a radiolabelled site of suspected tumor, is located at a shallow depth beneath overlying tissue by making use of the fact that the characteristic x-rays of the radiotracer only travel a short distance through tissue. For example, the characteristic x-rays of Technetium 99m have a half value layer of 8 millimeters, i.e., the number of 19-keV x rays of Technetium will drop by half through 8 millimeters of water.

The "very near-field" of the disclosed embodiment of this invention can be defined as two half value layers of water-equivalent tissue, wherein the received number of characteristic x-ray photons will be 100% to 25% of the number emitted. The "intermediate-field" can be defined as being tissue lying at depths greater than two, but less than four, half value layers beneath the exposed or exterior tissue plane, wherein the received number of photons will be from 25% to 6% of the number emitted. As discussed before, the very near field and the intermediate field together constitute the near field. The "far-field" can be defined as being located at or beyond four or more half value layers from the site of nuclear uptake for the characteristic x ray(s) of interest. In the far field the detected number of characteristic x rays will be very small, less than 6% of the number of characteristic x rays emitted from uptake sites at tissue depths greater than four half-value layers. Thus, for Technetium 99m the very near-field (or two half value layer) distance is approximately 0–17 mm, the intermediate-field is 17–33 mm, the near field (including both the very near and the intermediate fields) is approximately 0–33 mm., and the far-field is beyond 33 mm.

It should be pointed out that other ranges for the very near-field, intermediate-field, and far-field can be used with the subject invention, and the range of each of the fields as given above is merely exemplary. Moreover, the very near-field, intermediate-field, and far-field ranges, being a function of the energy level of the radiotracer, differ from radiotracer to radiotracer. For example, Indium 111 emanates characteristic x-ray photons at an energy of 24 keV, and at an abundance of 83.5%. Thus, if the same definitions are used as were given in the foregoing example, the very near-field for Indium 111 would be 0–27 mm, the intermediate-field would be 27–54 mm, and the far-field would be beyond 54 mm.

As mentioned above, the window setting means 30K of the instrument 24 serves to electronically select for evaluation a specific energy range or portion of the photons detected that falls within the probe's field-of-view 12. That is, by adjusting the window setting means, the practitioner can elect to examine only photons falling within a predetermined range of energies, i.e., select only characteristic x-ray photons which originate from tissue lying at shallow depths within the tissue (near-field radiation), or select a combination of the characteristic x-ray photons and the full energy gamma-ray photons which originate from tissue within the near-field. By using both the window-setting means and the ratio-calculation means the practitioner can select only the full energy gamma-ray photons which originate from tissue beyond the intermediate-field, i.e., with the far-field.

The window setting means is implemented by adapting the previously mentioned software in ways known in the art to enable the practitioner to select one or more of many preselected ranges of energy levels in order to evaluate only characteristic x rays of one (or more) energies and/or full-energy gamma rays of one (or more) energies from those detected by the probe 22, and thereby select and display data for photons emitted from one (or more) particular preselected range of tissue depths. For example, in accordance with one mode of operation of the present invention, in the case where a practitioner believes that an area of specific uptake may be located close to the surface of the overlying tissue, by adjusting the instrument's window setting means 30K, the practitioner can suppress information on extended field gamma-ray photons which cause ambiguity, and thus evaluate only characteristic X-ray photons that originates from points located only in close proximity to the exterior or external tissue surface (from the near field), e.g., often no more than ten (10) to thirty (30) millimeters deep. By using the signals from these characteristic x-ray emissions in ways to be discussed later, the practitioner is able to determine with a considerable degree of certainty the locations of cancerous tissue lying at shallow depths. In this way, by using radiotracers which emit gamma rays that have energies greater than 60 keV ("imaging radiotracers"), which can be used to form images in gamma cameras, and which also emit characteristic x rays of lower energies, the practitioner can have the following benefits. The practitioner can have pre-therapy gamma camera images, to assist in the search for sites of specific uptake, and also use a radiation detecting means during therapy to locate sites of uptake at shallow tissue depths, without having the search for said shallow sites compromised by signal from far-field radiation, such as background radiation from deeper sites of uptake.

In order to accurately localize near-field suspected tumors the instrument 24 may make use of the ratio calculation means 30N. For any radioisotope, the ratio of gamma rays to x rays is known and constant; in instances of a plurality of either gamma rays or x rays from a specific radioisotope, each such ratio between gamma rays or x rays of one energy and the gamma rays or x rays of another energy are likewise known and constant. The ratio detected from a specific radioisotope as the radiation passes through different thicknesses of tissue changes, in accordance with the absorption of photons of differing energies as they pass through a substance, as described on page 21. These known ratios are stored in the instrument in the aforementioned reference library. For example, Technetium 99m provides a natural abundance of 7.5% 19-keV characteristic x-rays and 89% 140-keV full energy gamma-rays. Indium 111 provides a natural abundance of 83.5% 24-keV characteristic x rays, 89.6% 172-keV full-energy gamma rays, and 93.9% 247-keV full-energy gamma rays. The ratio calculation means 30N serves to calculate the ratio of characteristic x rays detected versus gamma rays detected within a given period of time for a particular radioisotope, and to compare that calculated ratio with the stored reference ratios for specific, different depths of tissue, and for no depth of tissue. For cases in which either no background radiation, or a low level of background radiation is detected within the field of view associated with a site of specific uptake located at a shallow depth, information based on this ratio can be used by the practitioner to more closely establish the depth of that site. The implementation of the ratio calculation means 30N is easily accomplished by modification of the aforementioned commercially available computer programs.

The subtraction calculation means 30P works in cooperation with the ratio calculation means 30N to provide additional depth (z-axis) information about tissue with nuclear uptake. In particular, the means 30P subtracts the number of detected full-energy gamma-rays which correspond to the number of detected x rays from the total number of detected full-energy gamma rays, to result in a measure of far-field radiation emitted by tissue lying at depths beyond that from which the detected characteristic x-rays were emitted. The far-field radiation may be from both non-specific background radiation and from specific uptake of deeper-lying tissue. The practitioner can use this information on far-field radiation, for example, to evaluate uptake in deeper tissues.

If the practitioner simultaneously uses more than one radioisotope in the radiotracer, or more than one radiotracer, each with a different radioisotope, where the relative uptake of the two radiotracers are known and predictable, then the ratio calculation means 30N and the subtraction calculation means 30P can be further used to obtain additional information on the depth of tissue with nuclear uptake. For example, if the radioisotopes to be used are Technetium 99m, which emits characteristic x-rays at approximately 19 keV, and Iodine 123, which emits characteristic x-rays at approximately 27 keV, then the 27 keV x-rays would be detected from tissue lying at greater depths than the tissue from which the 19 keV x-rays were detected. By using the same methodology discussed above in connection with the subtraction means, the radiation detected can be divided into Technetium 99m near-field (emitted by tissue from which 19-keV x rays are detected), Technetium 99m-Iodine 123 intermediate field (emitted by tissue from which 29-keV x rays are detected but not 19-keV x rays), and Iodine 123 far field (emitted by tissue from which gamma rays are detected but not 29-keV x rays). The practitioner can then use this information, for example, to further establish the depth and thereby better establish the lateral X, Y location and depth Z coordinates of the various tissues in which the uptake is found.

The same method may be used to further segment the depth of the radiation field, by using radioisotopes exhibiting more than one gamma and/or characteristic x-ray peak, wherein the photon energies generally involved lie below about 100 keV; an example of one such radioisotope is Thallium 201, which emits x-rays at about 70 and 81 keV. By applying the ratio calculation means together with the subtraction calculation means to a multiplicity of x-rays and/or gamma-rays, the invention allows the practitioner to further segment the depth of the layers of tissue in which uptake is detected, and thereby more closely locate the tissue uptake site(s) of interest.

In accordance with a preferred embodiment of this invention, the instrument 24 also includes the heretofore identified spectral line shape recognition means 30Q. As is known, the numbers of photons detected, or the numbers of counts, in the characteristic x-ray and gamma-ray peaks for a particular radioisotope are dependent upon several factors, including the density and atomic number of material through which photons must travel prior to detection, e.g., blood, soft tissue, lung tissue, or bone, and the distance the photons must travel through that material prior to being detected by the probe 22. Soft tissue, blood, and most tumors have similar densities, i.e., approximately that of water. Bone is much denser. Lungs, because of their large air content, have effective densities much less than water. Therefore, when gamma-ray photons and x-ray photons travel through relatively dense materials, e.g., bone, prior to detection, the attenuation will be disproportionately high for the lower energy x rays. In this regard the linear attenuation of bone at 20 keV is approximately nine times that of muscle, while muscle is very close to water in linear attenuation. Consequently, the number of x-ray photons detected will be relatively low or non-existent when passing through bone. Conversely, when x-ray and gamma-ray photons travel through less dense materials, e.g., soft tissue, the number of characteristic x rays detected and displayed in the spectrum will be relatively high. The typically higher energy gamma rays will suffer similar attenuation effects, but to a lesser degree.

By storing in the instrument 24 a library of reference data representing the line shapes of the spectra for various radioisotopes, as a function of the thickness and types of intervening tissues, as discussed on page 34, the instrument 24 is able to provide the practitioner with information to localize the suspected tumor.

Figure 12:
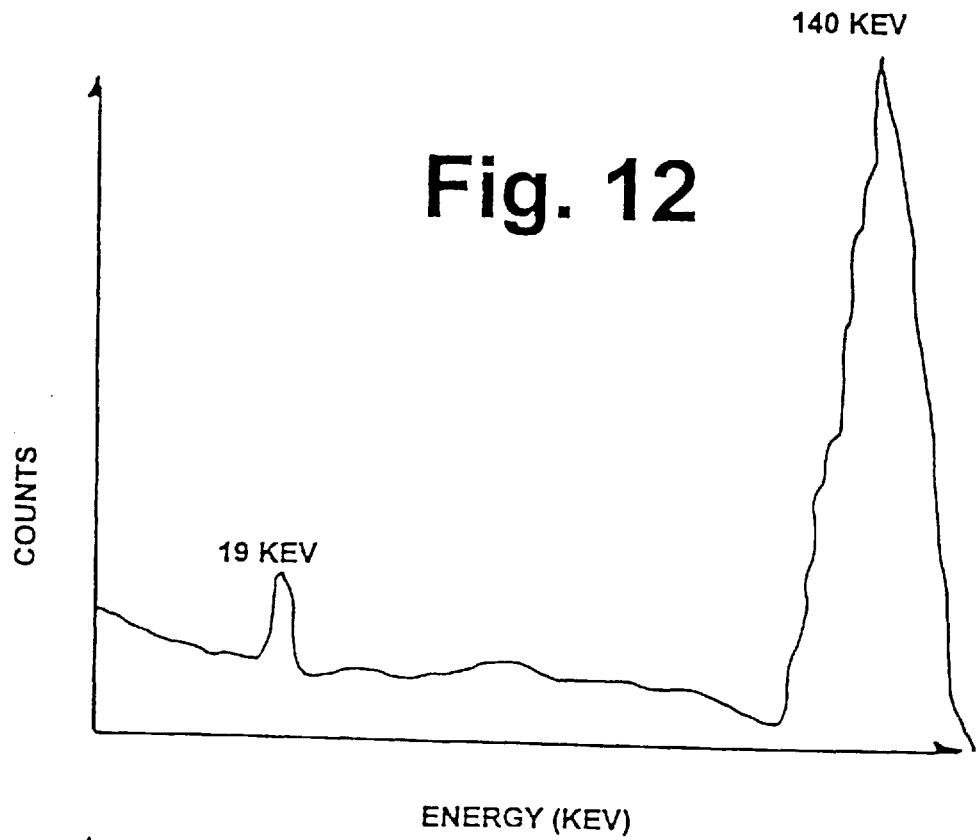
FIG. 12 is an exemplary graphical representation or histogram of the spectrum of the radiation counts obtained by the system of FIGS. 1A and 2 from a Technetium 99m radiotracer through air.
Figure 13:
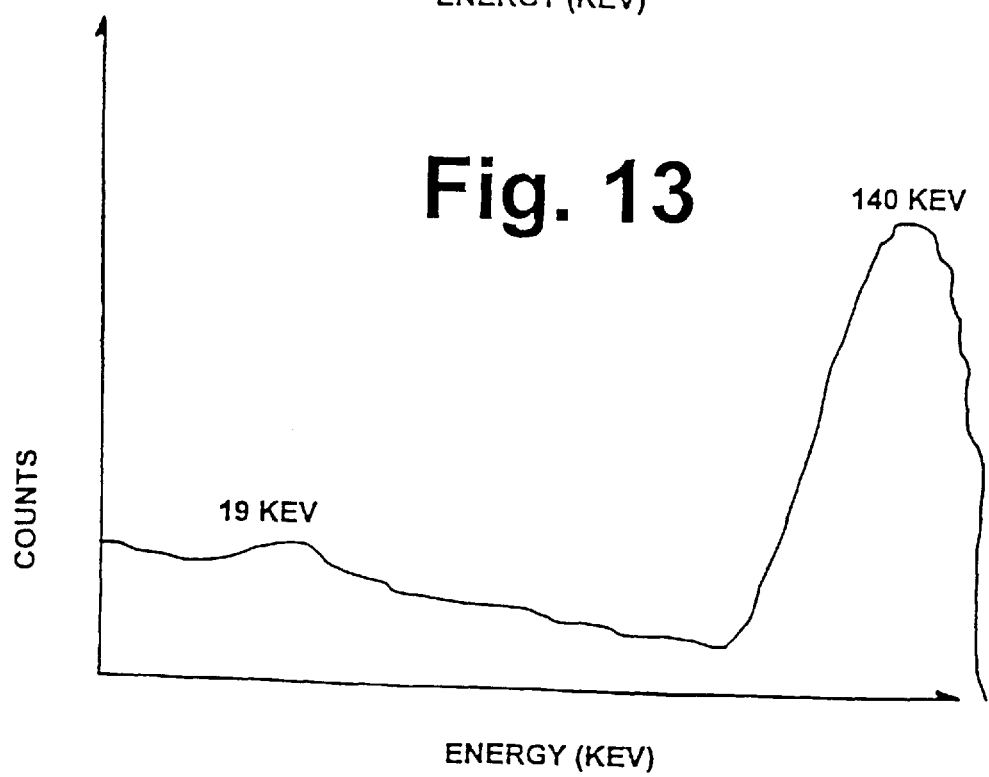
FIG. 13 is a histogram, like that of FIG. 12, but of the radiation counts received through a reference distance of water equivalent tissue.

In FIG. 12 there is shown the spectra of photons from a Technetium 99m tagged source passing through air to a probe a predetermined distance away. FIG. 13 represents that spectrum with a known material, e.g., water (to represent water equivalent tissue), of a known thickness therebetween. As can be seen, the trailing or lower energy edge of the full energy gamma-ray photopeak has become asymmetrical and wider, and the maximum of the peak has been reduced. The data representing both of the spectra of FIGS. 12 and 13 as well as other data for other thicknesses of intervening body materials, e.g., muscle, tissue, bone, lung, etc., are stored in the reference library in the instrument 24. These data are used by the line shape recognizing means 30Q to compare to the spectrum of the photons actually detected by the probe 22 and processed by the multichannel analyzer and associated means described above. In particular, the line shape recognizing means looks for the closest fit, and once that is achieved the instrument 24 provides the practitioner with information visually on the display screen 30F and/or audibly by the annunciator 30G on the depth of the tissue exhibiting the detected specific nuclear uptake. Thus, by examining the degree of asymmetry of the gamma-ray peak actually measured to that of the reference library, the depth of tissue of known density above the site from which the photons were emitted is determined.

The practitioner may make use of the increase in gamma-ray or x-ray peak line shape asymmetry as tissue depth or density through which the gamma-rays or x-rays pass increases. In this regard, if the distance to the site of specific uptake is known or can be estimated to a reasonable degree of assurance by some independent means, then by using the data in the stored reference library, the instrument may provide the practitioner with information for estimating density of tissue intervening between the site of specific uptake and the probe. One example of the use of density information would be for a site of uptake known to be at a shallow depth, such as a tumor penetrating from within the bone marrow cavity, through to the surface of the bone. Such determinations could be of great benefit in optimizing use of electron beam and other high linear energy transfer radiation therapies.

The spectral line shape measurements which are made to establish the reference data for use by the spectral line shape recognizing means 30R can be made with solid state semiconductor detectors, such as Cadmium Zinc Telluride, Silicon, or Germanium, at room temperature or cooled below room temperature.

As discussed earlier the instrument 24 is equipped with the annunciator 30G. The annunciator is driven by the annunciator driver 30T to provide audible signals to aid the practitioner as he or she uses the probe to localize the suspected tumor for radiation therapy. In particular, the driver 30T drives the annunciator to cause it to provide audible sounds which are modified in various ways, e.g., in pitch, in intensity, in repetition rate, or in some other way or combination of ways, as a function of the rate at which the characteristic x-ray photons and/or full-energy gamma-ray photons are being detected. The sound production provided by the annunciator 30G is known in the prior art and has been available on several different commercially available surgical gamma probe systems. The driver 30T for the annunciator may be implemented by any suitable software. For example, when the invention is being used to detect characteristic x rays exclusively, the annunciator's driver 30T may be set to emit a specific form of signal, e.g., "beeps", only upon detection of characteristic x-ray photons by probe 22. Specifically, when the probe 22 is directed toward a volume wholly comprised of clean tissue, i.e., away from a location of specific uptake, the probe 22 will detect a relatively low rate of characteristic x-ray photon emissions (because only a relatively dilute concentration of radiotracer will exist within the probe's field-of-view). Therefore, the annunciator 30G will emit beeps at a slow rate indicating that probe is detecting clean tissue only.

Conversely, when probe 22 is directed toward a shallow site of specific uptake i.e., a location containing cancerous tissue, the probe 22 will detect characteristic x-ray photons emitted at a greater rate as the result of a higher concentration of radiotracer existing at the site of specific uptake. Thus, the beeps emitted from the annunciator under the control of driver 30T will change dramatically in frequency, thereby indicating that a site of suspected specific uptake has come within the field-of-view of probe.

In an alternative embodiment, the annunciator 30G under the control of its driver 30T can produce tones and/or chirps to be utilized alone or in conjunction with beeps to audibly distinguish areas of suspected specific uptake from areas of clean tissue. The annunciator driver may be arranged so that it can be adjusted by the practitioner to cause the annunciator to emit beeps upon the detection of lower energy (typically characteristic x-ray) photons and simultaneously to emit chirps or other audibly distinguishable tones upon the detection of higher energy (typically gamma-ray) photons. If desired a voice synthesizer can be used to provide verbal information to the practitioner.

The method of use of the system 20 to localize a suspected tumor site tagged with Technetium 99m will now be described with reference to FIGS. 3–11.

To determine the location of Technetium 99m tagged lesions lying at shallow depths below the exposed or external tissue plane, i.e. within the "near-field", one can examine the characteristic x-ray photons while ignoring the gamma-ray photons being received. By examining these photons, the system enables the user to center the probe over a near-field site of uptake, e.g., a suspected tumor or lesion.

To determine the location of Technetium 99m tagged lesions lying at shallow depths below the exposed or external tissue plane, i.e. within the "near-field", one can examine the characteristic x-ray photons while ignoring the gamma-ray photons being received. By examining these photons, the system enables the user to center the probe over a near-field site of uptake, e.g., a suspected tumor or lesion.

To determine the location of suspected tumors in the near field, especially in the deeper (or intermediate) portion of the near field, the radiation therapy practitioner can also use the system of this invention to examine both the characteristic x-ray photons received and the full-energy gamma-ray photons received, and compare numbers of each detected, thereby obtaining information regarding the depth of the suspected tumor within the near field.

In addition, to determine the location of suspected tumors deeper within the tissue, i.e. within the "far-field", the system of this invention can examine the number of full energy gamma-rays detected, and subtract the number of detected gamma rays which correspond to the number of characteristic x-rays detected for the radioisotope in use, resulting in a count of gamma rays originating from the far-field only, from tissue depths from which no emitted characteristic x rays can be detected.

Uptake in normal tissues, such as kidney uptake of Technetium 99m labelled radiopharmaceuticals, prevents blind application of the technology of this invention. The radiation therapy practitioner must designate the areas of uptake that are used to guide therapy. Uptake in kidneys and other vital normal organs can help demonstrate the likely deposition of the therapy beam's energy in vital structures during the therapy planning phase, thereby reducing inadvertent injuries.

Of significant importance to this invention is the fact that the skilled practitioner is able to determine whether the gamma-ray photons received are from a distant normal tissue uptake source, e.g., a kidney within the probe's field of view, or from a nearby radiolabelled source, e.g., a possibly cancerous lymph node, within the probe's field of view. In this regard, if the proportion between the characteristic x-ray photons received to the gamma-ray photons received is appropriate for a nearby source then one can rely on the statistics of the nearby gamma-ray photons received. In this regard, as mentioned above, the 19-keV characteristic x rays of Technetium 99m have an abundance of 7.5%, and the 140-keV full-energy gamma-ray photons have an abundance of 89% Thus, the ratio of the natural abundance of characteristic x-ray photons to full energy gamma-ray photons is 7.5/89 or 0.084. Accordingly, if the ratio calculating means of the system detects a sufficient number of characteristic x-ray photons such that their ratio to the gamma-ray photons detected is 0.084, then the practitioner knows that both the gamma rays and the x rays being received are from a radiolabelled source lying at a shallow depth beneath the exposed tissue plane, and not from a deep source of uptake.

As noted earlier, the display panel 30F shows the number of characteristic x-ray photons and full-energy gamma-rays received by the lengths of the lighted portion of the light bars 32A and 32B, respectively, and by the associated numeric displays 34A and 34B, respectively. The light bars in this case are normalized for the appropriate ratio of characteristic x-ray photons to full gamma-ray photons for the radiotracer utilized, e.g, a ratio of 0.084 for Technetium 99m, so that when an appropriate ratio of characteristic x-ray photons and full energy gamma-ray photons are received the lighted portions of the light bars will be of the same length, while the associated numeric displays show numerically the absolute number of photons detected during the measurement or "count" period. The annunciator, in response to the driver 30T, produces respective sounds representing the rates at which the characteristic x-ray photons and full energy gamma-ray photons are detected. These sounds can be normalized by the annunciator driver, if desired.

The radiation therapy practitioner can use the displays and/or sounds produced to determine the location of the radiolabelled tissue. For example, assume that the radiation therapy practitioner is trying to localize a suspected tumor or lesion within the abdomen of a patient who had received a radiolabelled tracer, e.g., a monoclonal antibody tagged with Technetium 99m. To accomplish that procedure the radiation therapy practitioner may move the therapy machine mounted probes 22 in the x, y, and z directions with respect to the suspected tumor site to find the probe location and orientation which yields the maximum number of characteristic x-rays detected, and compares the ratio of the two numbers to that expected for the radiotracer used. This procedure is graphically represented by the illustrations of FIGS. 3–9.

Turning now to FIG. 3, it can be seen that there is illustrated the situation wherein the nose or tip 22A of the probe 22 is located in immediate proximity to the front surface of a radiolabelled site of suspected tumor, with the tumor being located within the probe's "field of view" (designated by the phantom lines).

The graphical representation of the number of characteristic x-ray photons received by the probe during the count period is displayed on the system's normalized light bar 32A, while the absolute number of photons detected is displayed on the associated numeric display 34A. In a similar manner a graphical representation of the number of full energy gamma-rays detected by the probe during the count period is displayed on the system's other normalized light bar 32B, while the absolute number of photons detected is displayed on the associated numeric display 34B. The annunciator, if enabled by its driver, will produce corresponding audible signals so that the practitioner need not look at the display panel 30F. If desired, the annunciator can be disabled so that no sounds are produced.

The following examples serve to illustrate the general methods involved in using radiation detecting means, as described by this invention, to locate sites of concentrated nuclear uptake. The actual numbers of photons detected must be sufficient to provide statistically significant data and thereby provide the practitioner with the appropriate level of confidence in said data, as described on page 26.

In the example of FIG. 3 the number of characteristic x-rays detected during the count period is 600 and the number of full energy gamma-rays detected is 7143. Thus, the ratio of the characteristic x-rays to the full energy gamma-rays is 600/7143 or 0.084. This ratio, being the ratio normally existing for characteristic x-rays and gamma-rays of Technetium 99m, and which is stored in the reference library of the instrument 24, indicates that the data received are appropriate to a radiolabelled source with little or no intervening tissue (i.e., the ratio calculation means compares the detected photons to the reference photons to determine if the proper ratio exists). The light bars 32A and 32B in this case will each be of the same length, thus graphically displaying that the appropriate ratio exists. Thus, the radiation therapy practitioner is justified in believing, from the displayed information (as well as audible sounds, if enabled), that a site of significant uptake, e.g., the radiolabelled site of suspected tumor, is probably within the field of view of the probe and in close proximity to the exterior tissue plane against which the probe's nose 22A rests.

By moving the probe 22 laterally up or down (i.e., in the "y" direction) and right or left (in the "x" direction) and taking readings of the characteristic x rays detected in a given time period, or count rate, until a maximum count rate is attained, the radiation therapy practitioner is able to center the probe on the suspected tumor site. In this regard, when the count rate for characteristic x rays is maximized, at any distance from a shallow site of uptake, or along a given tissue plane, the axis of the probe will be aligned with the center of the that site, as determined by the measured amounts of nuclear uptake. Thus, by maximizing the count rate for characteristic x rays at any tissue plane at which the nose of the probe is located, one is able to establish the "x" and "y" coordinates of the center of a proximate suspected tumor for any given distance from that tissue plane.

Moreover, the count rate for characteristic x-rays in comparison to the count rate for full-energy gamma rays provides some indication of the distance, i.e., the "z" coordinate, from the front surface of the suspected tumor to the exterior tissue plane.

With many radiotracers, such as those involving monoclonal antibodies, there are known, predictable locations of significant non-specific uptake. The following examples are based on conditions wherein the surgeon would know that the kidneys would be such sites of significant non-specific uptake.

As should be appreciated by those skilled in the art, if, in attempting to localize a radiolabelled site of suspected tumor, the system 20 of the subject invention detects a number of characteristic x-ray photons which is disproportionately low relative to the number of gamma-rays for the radioisotope being used, then the radiation therapy practitioner would be justified in believing that the vast majority of the gamma-rays detected are emanating from distant, or far off, intense sources of uptake, deep within the tissue, rather than close-in areas of uptake, i.e., the suspected tumor. An example of this condition is shown in FIG. 4, wherein the probe 22 is shown centered over a Technetium 99m tagged suspected tumor in a lymph node located very close to the nose of the probe, and with a substantial portion of the patient's kidney being in the probe's field of view, but significantly remote or deep within the tissue, e.g., five cm from the nose of the probe. Since the kidney typically absorbs a significant amount of the radiolabelled tracer, and in this example is five cm beneath the exposed tissue plane, the characteristic x-rays from the kidney have to pass through six half value layers of intervening water-equivalent tissue, whereupon only 1% of those x-ray photons reach the probe. The vast majority of the characteristic x-ray photons received by the probe, e.g., 600 in this example, will be from a nearby uptake source, in this case the suspected tumor. Since full energy gamma-ray photons are able to travel through much greater distances of intervening tissue without significant attenuation or absorption than are the x-rays, the number of the gamma-ray photons received will be quite high relative to the number of characteristic x rays received. In this example 20450 gamma-rays are detected. The resulting ratio of numbers of characteristic x-rays detected to numbers of gamma-rays detected is thus 0.029. This disproportionately low ratio is graphically represented by the normalized light bars being of different lengths, i.e., as can be seen in FIG. 4 the light bar 32B representing the gamma-rays is substantially longer than the light bar 32A representing the characteristic x rays, to indicate to the surgeon that the vast majority of the gamma-ray photons being received are probably from a remote, intense site of uptake (in this case a substantial portion of the kidney, the general location of which will be known to the radiation therapy practitioner).

Hence the radiation therapy practitioner must continue his/her search to maximize the numbers of characteristic x-rays detected in the desired ratio to the number of gamma rays detected in order to localize the suspected tumor. To achieve that end the radiation therapy practitioner can move the probe laterally along the exposed tissue plane, to the right and/or left (i.e.,in an "x" direction) and up and/or down (i.e., in the "y" direction) from its previous "on axis" position to take "off axis" control readings, and thus determine how the detected numbers of photons change. This enables the radiation therapy practitioner to locate the marginal edges of the suspected tumor, and to compare numbers of photons detected from the suspected tumor to those from the adjacent background. For example, as shown in FIG. 5, if the probe is moved to the left until the numbers of detected characteristic x-rays drop dramatically, e.g., drop from 600 to 30, while the numbers of detected gamma-rays drop from 20450 to 10060, this indicates that the suspected tumor is no longer within the probe's field of view, while a lesser (but still a considerable portion) of the remote area of uptake (e.g., a lesser portion of the kidney) remains within the field of view.

Figure 6:
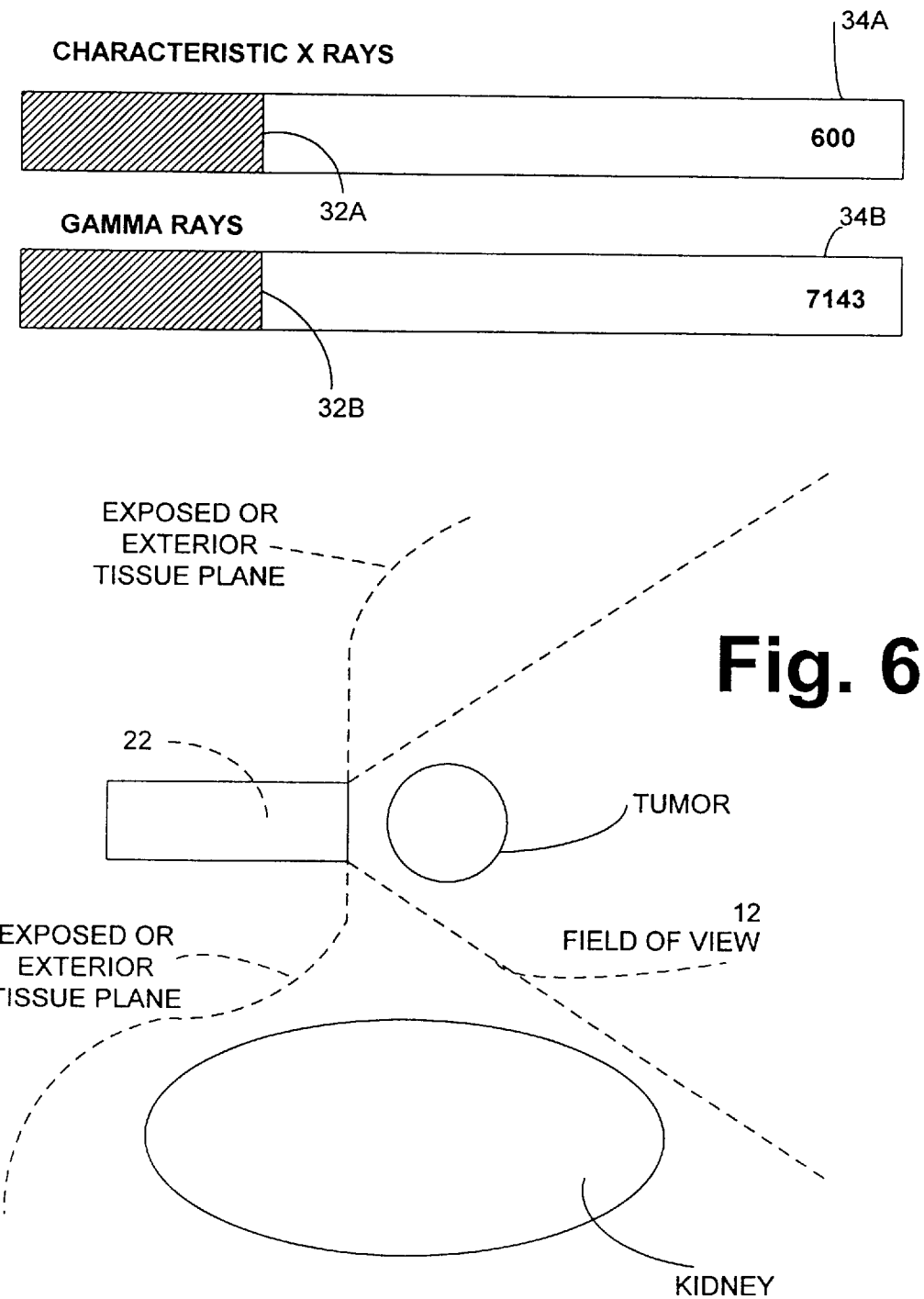
FIG. 6 is an illustration, like that of FIG. 5, but showing the system of FIGS. 1A and 2 being used in yet a later step of determining the location of the radiolabelled tumor of FIG. 4.
Figure 7:
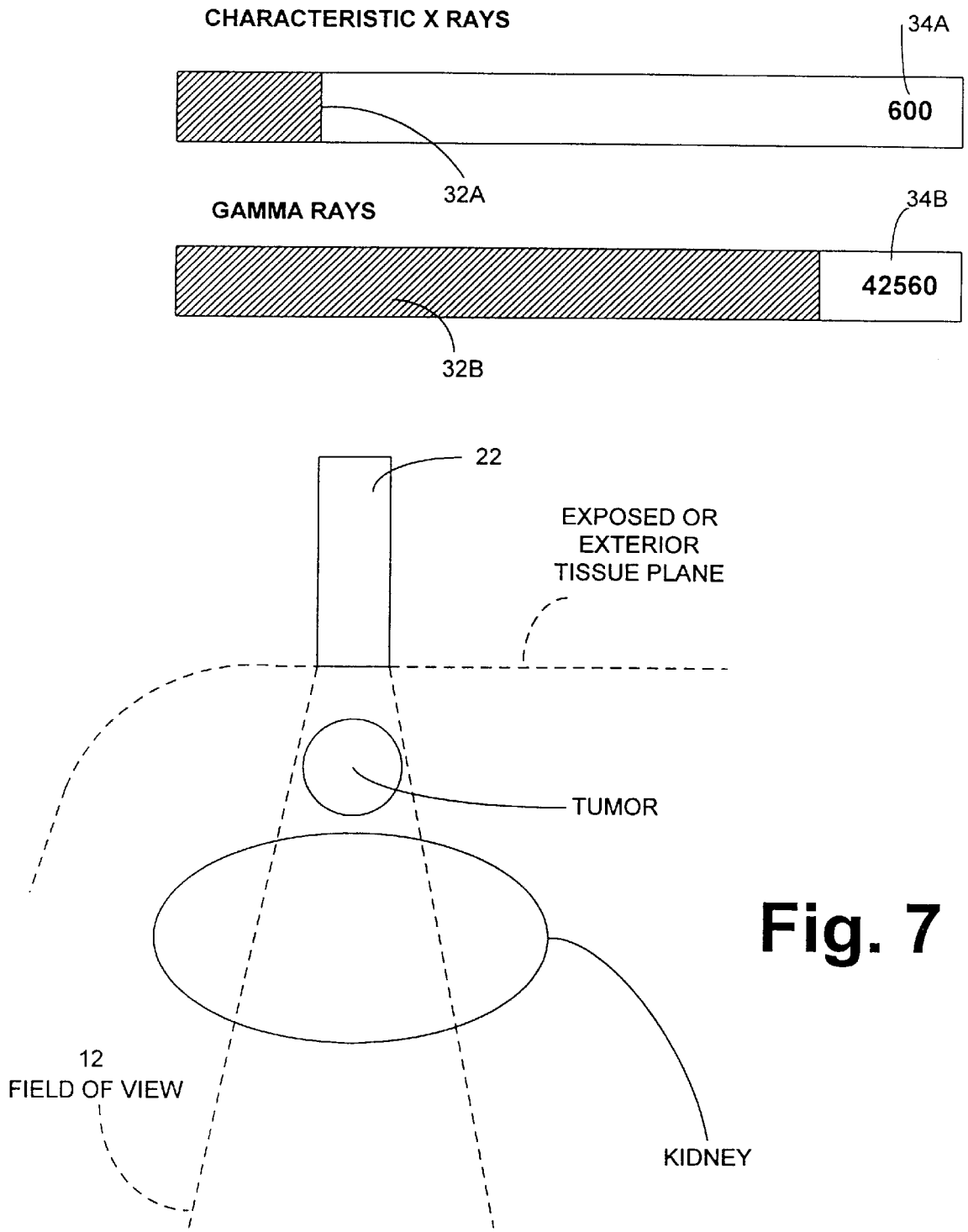
FIG. 7 is an illustration, like that of FIG. 3, but showing a portion of the system shown in FIGS. 1A and 2 being used to determine the location of a radiolabelled tumor located immediately adjacent kidney in accordance with one aspect of the method of this invention.

The radiation therapy practitioner then has to continue the search to localize the suspected tumor. To that end, if the radiation therapy practitioner moves the probe in the "x" direction to the left of the tumor, down in the "y" direction so that the suspected tumor is out of the probe's field of view (whereupon the numbers of characteristic x-rays detected in a given time period will drop dramatically) and then orients the probe at an angle to its original orientation until the numbers of detected characteristic x-rays increase dramatically and the numbers of detected gamma-rays drop dramatically, the radiation therapy practitioner is able to "home in" on the suspected tumor by eliminating the effects of the remote site of uptake, i.e., the kidney, thereby establishing an appropriate angular orientation for therapy. This action is illustrated in FIG. 6, wherein the probe is shown oriented perpendicular to its original orientation so that 600 characteristic x-rays are detected, while 7143 gamma-rays are detected. In this case, the light bars 32A and 32B will be of the same length since the ratio of x-rays to gamma-rays is 0.0840 thereby indicating the presence of a close uptake source, i.e., the lymph node with suspected tumor, with no other source of uptake (i.e, no portion of the kidney) in the field of view. The radiation therapy practitioner is thus able to localize the suspected tumor and determine the optimal therapy beam orientation for attacking the suspected tumor, while sparing adjacent vital organs.

Figure 8:
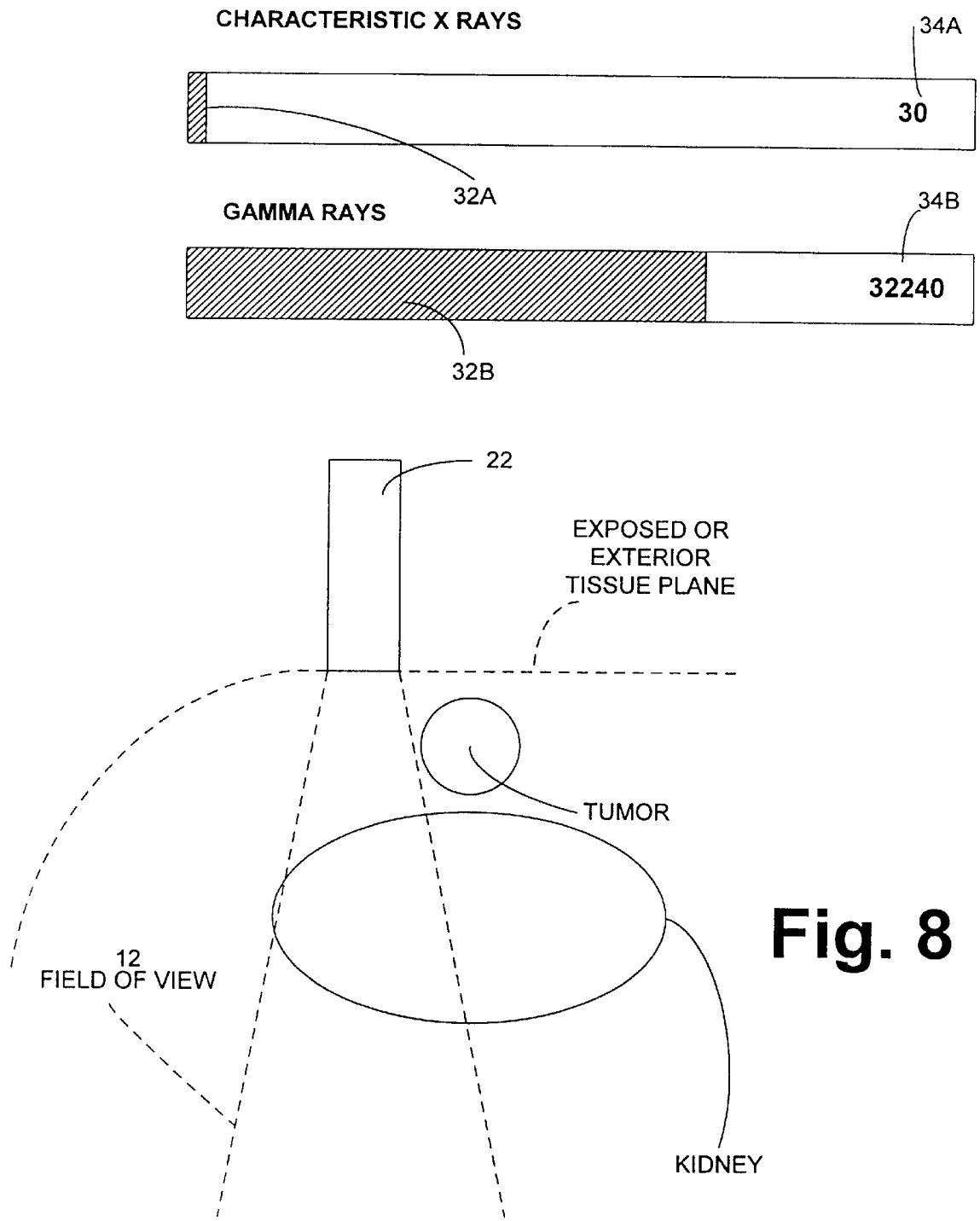
FIG. 8 is an illustration, like that of FIG. 7, but showing the system of FIG. 1A and 2 being used in a later step in determining the location of the radiolabelled tumor of FIG. 7.

As mentioned earlier, the probe 22 preferably includes a collimator 22E. That collimator may be adjustable or fixed, in order to decrease (or increase) the field of view of the probe's radiation detector or crystal 22C to facilitate the localization of the suspected tumor, e.g., to restrict the probe's field of view, thus making it easier for the surgeon to avoid detecting known sources of non-specific uptake. This feature may be of significant assistance in localizing suspected tumors, particularly those closely adjacent to intense sources of known non-specific uptake. For example, in FIG. 7 there is illustrated the localization of a suspected tumor much closer to the kidney than in the example described with reference to FIG. 4. In this latter example 600 characteristic x-rays are detected, while 42560 full energy gamma-rays are detected. The ratio of characteristic x-rays to gamma-rays in this case being disproportionately small indicates to the radiation therapy practitioner that there is an intense deep source of uptake in the probe's field of view, from which only gamma rays are detected, as well as a closer source of radiation from which x-rays are detected. Thus, the radiation therapy practitioner should continue the search in a similar manner to that described earlier. In particular, moving the probe to the left as illustrated in FIG. 8 until the numbers of detected x-rays drop to 30, while the number of detected gamma-rays drop to 32240 indicates that the suspected tumor is no longer within the probe's field of view, but that a deep source of uptake still is. By orienting the probe similarly to that shown in FIG. 6 and by narrowing the probe's field of view as shown in FIG. 9 by using the collimator 22E on the probe 22, the radiation therapy practitioner is able to detect 300 characteristic x-rays and 9450 full energy gamma-rays, whereupon the radiation therapy practitioner is justified in believing that there probably is no other source of non-specific uptake in the probe's field of view. He or she can further substantiate the location of the suspected tumor by keeping the probe at the same orientation and observing the displays as the probe is moved in different directions along the plane. Thus, the suspected tumor is localized.

Figure 10:
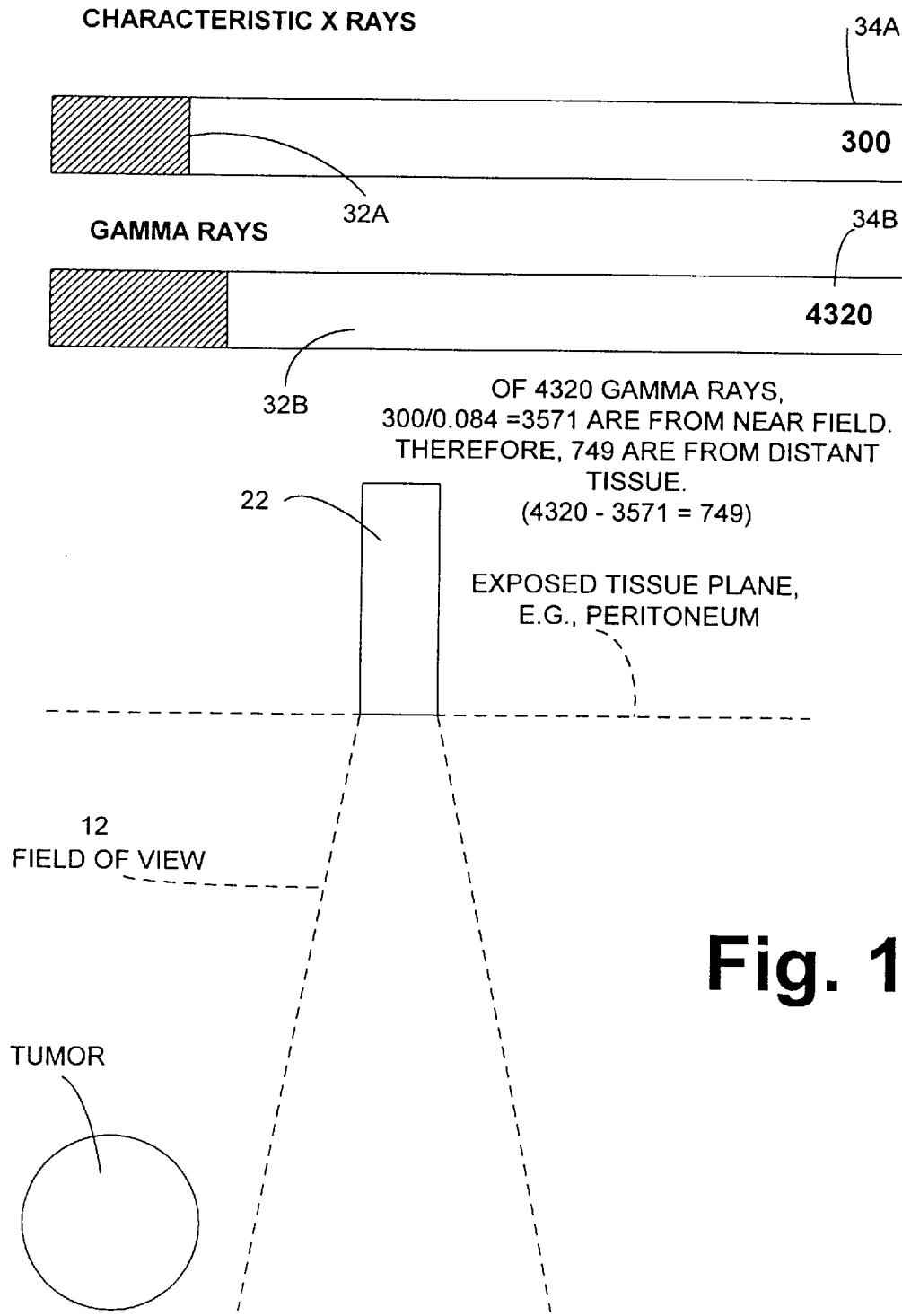
FIG. 10 is an illustration, like those of FIGS. 3A and 3B, but showing a portion of the system shown in FIGS. 1A and 2 being used to determine the location of a radiolabelled tumor located deep within the abdomen in accordance with one aspect of the method of this invention.
Figure 11:
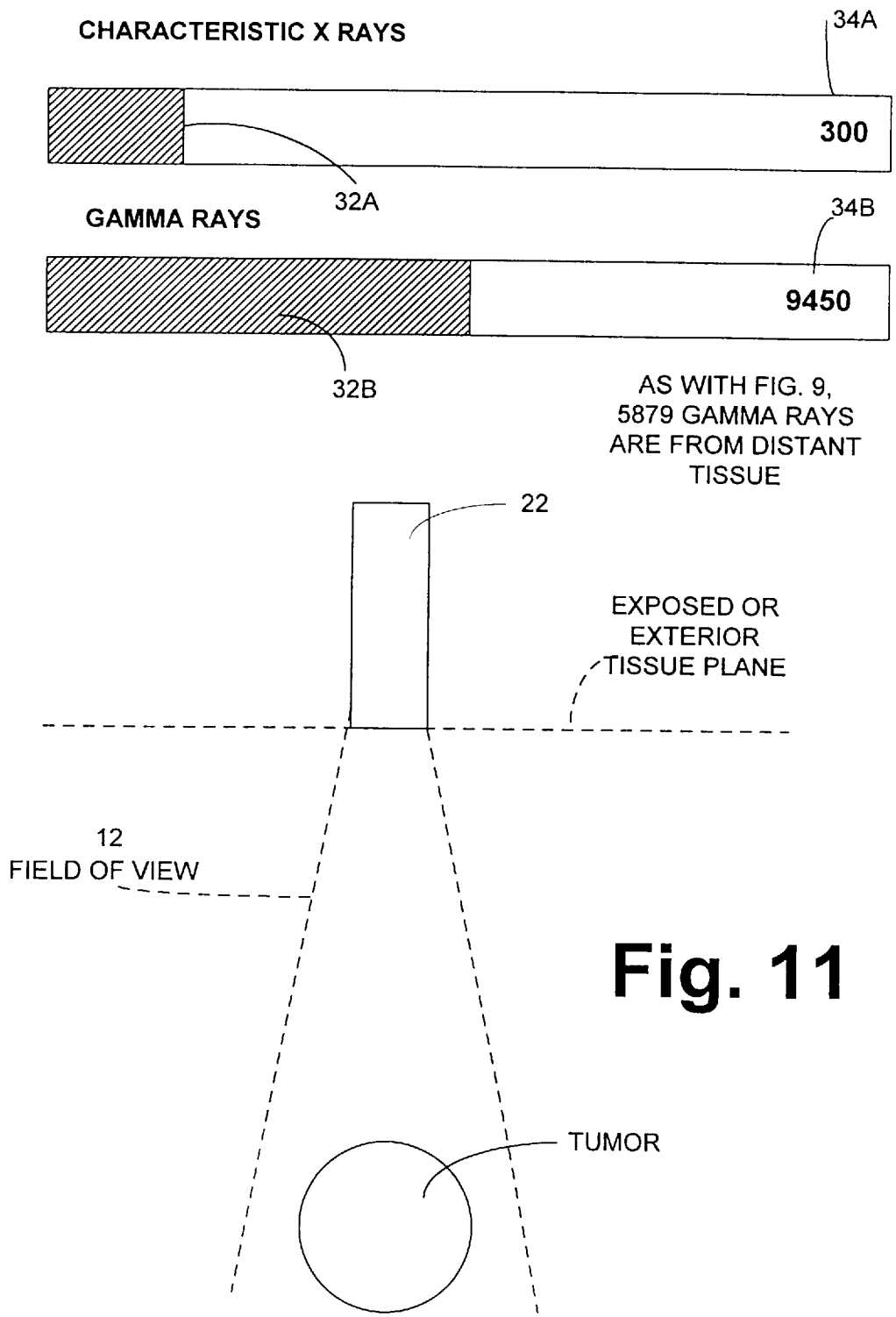
FIG. 11 is an illustration, like that of FIG. 7, but showing the system of FIGS. 1A and 2 being used in a later step in determining the location of the radiolabelled tumor of FIG. 10.

In order to localize a specific uptake source, e.g., a suspected tumor, located beyond the near-field for the specific radioisotope used, the system 22 makes use of the detected full energy gamma rays. However, the characteristic x-rays received are also utilized to determine if the ratio of characteristic x-rays to the full energy gamma-rays is appropriate so that the numbers of detected gamma-rays can be used to indicate a distant source of specific uptake. In FIGS. 10 and 11 there is illustrated a process of localizing a Technetium 99m tagged suspected tumor site located deep within the abdomen of an obese person, and assuming that it is desired not to penetrate the peritoneum tissue plane with the probe 22 to localize the suspected tumor. Thus, in this case the suspected tumor will be beyond the near-field.

In FIG. 10 the probe is illustrated as being off axis of the suspected tumor, with the system detecting 300 characteristic x-rays and 4320 full energy gamma-rays. The light bars 32A and 32B in this case will not be of equal length since the ratio of characteristic x-rays to full energy gamma-rays will be disproportionately low. In addition, when the radiation therapy practitioner moves the probe to locations adjacent to that shown in FIG. 10 in any direction other than that which moves it over the suspected tumor, the relative numbers of detected gamma rays and characteristic x rays will not appreciably change. Thus, the radiation therapy practitioner is justified in believing that the detected radiation probably represents background radiation from low concentration uptake generally present throughout the tissue, and further searching must be conducted to localize the tumor. To achieve that end the probe is moved in either the x or y direction (left/right or up/down, respectively). In the illustration of FIG. 11 the probe is shown having been moved in the x direction to the left until the numbers of detected gamma rays increase. In this example the numbers of detected characteristic x-rays remain at 300, since the source of x rays remains the tissue close to the probe, with the low concentration of uptake. However, the numbers of detected gamma-rays increase to 9450 when the probe is on axis (i.e., centered) with the suspected tumor, and then decrease as the probe is moved in any direction away from the suspected tumor such that the suspected tumor is again out of the field of view of the probe. Since the radiotracer being used has been tagged with Technetium 99m, for a reading of 300 characteristic x-rays there would be an associated 3571 full energy gamma-rays, if there were no tissue intervening between the site of uptake and the radiation-detecting probe. Therefore, from the readings received the radiation therapy practitioner is justified in believing that 5879 gamma-rays (9450–3571) are probably coming from deeper, far-field sources of uptake, which he/she may know from anatomical knowledge to include a possible tumor, located beyond the near-field. Moreover, from the gamma-ray reading when the probe was off axis (FIG. 10) the radiation therapy practitioner is able to determine that of the 4320 gamma rays detected, 749 (4320–3571) probably represent other deeper, far-field sources of uptake, which could represent background from non-specific uptake such as that in blood pool, extracellular fluid, etc., from within the field of view of the probe.

If one were only to examine the numbers of detected gamma rays of FIGS. 10 and 11, as has characterized the prior art, and not separately take into account the numbers of detected characteristic x-rays and their ratios to the numbers of detected gamma rays, the ratio of suspected distant tumor gamma rays detected (the numbers of detected gamma rays of FIG. 11 when the probe is "on axis") to the background radiation detected (the numbers of detected gamma rays of FIG. 10 when the probe is "off axis") is 9450/4320. Thus, using the prior art examination of only gamma-rays results in a suspected tumor-to-background ratio of 2.19. However, using the system 20, the ratio of distant far-field gamma rays detected to the background gamma rays detected is 2879/749 or 7.85. This significantly higher tumor-to-background or contrast ratio provides the radiation therapy practitioner with a much better confidence level that the suspected tumor has, in fact, been localized.

Figure 15:
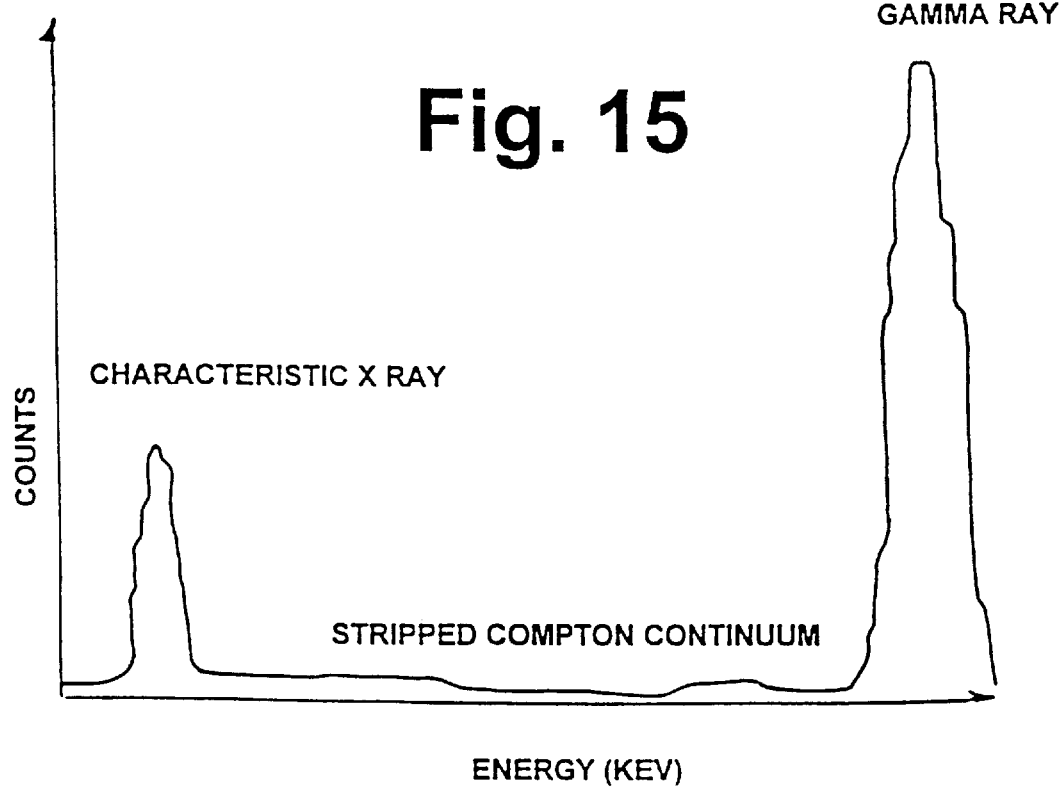
FIG. 15 is a histogram, like FIG. 14, but showing the spectrum of radiation counts obtained by the system of FIGS. 1A and 2 during the localization of the tumor in accordance with another and option aspect of this invention to remove the effects of Compton scatter in the measured readings of radiation detected.

As mentioned earlier, in many instances it is desirable that the numbers displayed represent the characteristic x rays and full energy gamma rays, but not any received Compton-scattered photons. This can be partially achieved by utilizing the collimator 22E on the probe 22 to minimize the number of Compton-scattered photons received. The goal may be more fully achieved by the characteristic x-ray isolation means 30L and the gamma-ray isolation means described earlier for substantially stripping or removing the signal representing the Compton continuum from the signal representing the spectrum of all photons received, to provide a processed signal representing primarily the characteristic x rays received and the full energy gamma rays received as shown in FIG. 15.

It must be reiterated at this juncture that while the removal of the signal representing Compton-scattered photons from the counts received is desirable, it is not mandatory. Thus, the system 20 need not remove data on Compton-scattered photons in order to enable the precise localization of specific uptake tissue.

It should be appreciated by those skilled in the art that the relative surface X, Y location and depth Z Cartesian coordinates of suspected tumor tissue established by this invention can be compared visually to gamma camera planar and three dimensional images. As a further refinement, absolute X, Y location and depth Z Cartesian coordinates of suspected tumor tissue established by this system can be correlated by computer with the corresponding absolute X, Y location and depth Z Cartesian coordinates of three dimensional gamma camera images previously obtained. Thus, a virtual map of the three dimensional distribution of suspected tumor tissue relative to the radiation therapy port which is coaxial with the probes positions and angular orientations (taking into account the probe's distance from the external tissue plane) can be tracked with feedback signals from appropriate commercially available x, y, z and angular orientation position sensing apparatus (not shown), attached to the probes.

In summary, the subject invention can utilize only the detection of short range, e.g., approximately 15–30 keV, characteristic x-rays as a signal in itself to guide the practitioner in orienting the probe to a site of near-field specific uptake. In addition, the detected characteristic x-ray signal, when compared to the associated full-energy gamma-ray signal, can also serve as an indication of the depth of origin of the detected gamma rays. When no angular orientation of the probe can provide substantially pure near-field signal of full energy gamma rays, the near-field signal alone can be electronically selected by using only the low energy characteristic x-ray signal. When, on the other hand, angular orientation of the probe indicates a high ratio of the number of detected characteristic x-rays to the number of detected gamma rays, demonstrating substantial near-field origin of the majority of the stronger gamma rays, then the number of detected gamma rays is accepted as indicating nearby uptake, i.e., radiolabelled tissue. When radioisotopes such as Technetium 99m are in use, wherein characteristic x-rays are much less abundant than full energy gamma rays it may be preferable to use the much stronger signal, with greater directional information, provided by the full-energy gamma rays.

For suspected tumors deeper within the tissue or within the "far-field", the practitioner using the system of this invention can electronically select only those detected gamma rays which originate from the far field, in order to localize the site of uptake.

In addition, as previously described, the system of this invention allows measurements of the line shape of detected full-energy gamma ray peaks to provide information on the depth of sites of uptake.

Thus, the subject invention provides the practitioner with the choice of whichever signal provides the greatest information according to the specific radiation therapy problem.

As discussed earlier previous attempts to define radiation therapy volume have predominantly relied upon fluoroscope or x-ray CT imaging options built into the therapy machine to allow simulation of tumor radiation dose. The use of internally administered tumor seeking radiopharmaceutical is fundamentally superior because of: simplicity, absolute co-axial registration, the possibility of both real time guidance and real time modulation of the beams, and the possibility of storing the initial real time data acquisition and registration data for subsequent treatments without the need to readminister the radiopharmaceutical. All prior art co-registration schemes attempt to find landmarks either innate within the patient or extrinsic to the patient and placed on the patient for co-registration purposes. The subject invention provides superior registration because the therapy-guiding data set is obtained from the metabolically active tumor at the time of the initial therapy. In this manner, extremely accurate patient registration can be achieved and the patient position can be confirmed with laser alignment beams so as to allow reproducible geometry when the patient returns for later therapy sessions without the need for an additional administration of radiopharmaceutical.

It is possible to use the 140.5 keV emission of Technetium 99m to model the performance of a higher energy emission beam so long as appropriate conversion factors are used. Using a phantom, it should be possible to obtain a map of the 140.5 keV emissions of technetium 99m and compare that map to a map provided by the 511 keV emissions of a similar size and configuration three-dimensional source of 511 keV photons in order to obtain an equivalence mapping. Once such an equivalence mapping has been obtained in a phantom, and validated in a small number of patients, then one could in general use the 140.5 keV signal from Technetium 99m to provide guidance for the external beam administration of significantly higher energy radiation beams.

The same nearly co-axial configuration of probe and emission port of a radiation therapy machine can be used for extremely high dose applications such as the "Gamma Knife." With very high dose radiation therapy machines, spreading the normal tissue dose becomes much more critical than it is with lower dose external beam radiation therapy procedures. Thus, the attenuation mapping becomes even more valuable than with conventional therapy machines.

The subject invention can be used in combination with systems (hardware and/or software) for producing a virtual reality, three dimensional map of the tumor in order to guide the probe(s) and/or therapy beam.

Without further elaboration, the foregoing will so fully illustrate my invention that others may, by applying current or future knowledge, adopt the same for use under various conditions of service.

What is claimed is:

1. A system for providing precise therapy radiation to living tumor tissue within the body of a living being, said system comprising a tumor localizing radiopharmaceutical, a controllable source of therapy radiation, and radiation detecting means, said tumor localizing radiopharmaceutical being attached to the living tumor tissue, whereupon said radiopharmaceutical produces tumor-localizing radiation from the living tumor tissue, said tumor-localizing radiation comprising photons of different energies, including gamma radiation, x radiation, and/or annihilation radiation, produced by said radiopharmaceutical, said controllable source of therapy radiation being arranged for providing at least one gamma or x ray or particulate therapy beam, said radiation detecting means being arranged to be brought into various positions adjacent the body of the being for detecting said tumor localizing radiation from a plurality of directions and utilizing the known naturally occurring abundance of emitted photons of different energies of said radiopharmaceutical as a reference factor to provide an indication of the three dimensional distribution of the living tumor tissue to which said radiopharmaceutical is attached and for providing a signal indicative thereof, said controllable source of therapy radiation being arranged for receipt of said signal to precisely direct said at least one beam of said therapy radiation to the living tumor tissue to which said radiopharmaceutical is attached, whereupon said at least one beam of said therapy radiation necrotizes that tissue with minimal damage to adjacent viable tissue.

2. The system of claim 1 wherein said controllable source of therapy radiation comprises means to direct said at least one beam of said therapy radiation to the living tumor tissue to which the radiopharmaceutical has attached from plural directions.

3. The system of claim 1 wherein said controllable source of therapy radiation comprises means to direct said at least one beam of said therapy radiation to the living tumor tissue to which the radiopharmaceutical has attached from plural directions.

4. The system of claim 3 wherein the energy of said at least one beam of said therapy radiation is a function of thickness and type of tissue intervening between it and the living tumor tissue to which the radiopharmaceutical has attached.

5. The system of claim 1 wherein said controllable source of therapy radiation comprises means which produces at least one beam of said therapy radiation whose energy is selectable.

6. The system of claim 5 wherein said means which produces said at least one beam of said therapy radiation is adjustable so that the energy of said at least one beam of said therapy radiation is a function of thickness and type of tissue intervening between it and the living tumor tissue to which the radiopharmaceutical has attached.

7. The system of claim 1 wherein said controllable source of therapy radiation comprises means to precisely direct said at least one therapy beam of said therapy radiation to the living tumor tissue to which the radiopharmaceutical has attached in automatic response to said electrical signal.

8. A system for providing precise therapy radiation to living tumor tissue within the body of a living being provided with a tumor localizing radiopharmaceutical attached to the living tumor tissue, the radiopharmaceutical emitting tumor-localizing radiation of different energies comprising photons of different energy, including gamma radiation, x radiation, and/or annihilation radiation, from the living tumor tissue to which said radiopharmaceutical has attached, said system comprising a controllable source of therapy radiation, and radiation detection means, said radiation detecting means being arranged to be brought into various positions adjacent the body of the being for detecting the emitted radiation from said radiopharmaceutical from a plurality of directions and utilizing the known naturally occurring abundance of emitted radiation of different energies of said radiopharmaceutical as a reference factor to provide an indication of the three dimensional distribution of the living tumor tissue to which said radiopharmaceutical is attached and for providing an electrical signal indicating the three dimensional distribution of the living tumor tissue to which the radiopharmaceutical is attached, irrespective of the location thereof within the body of the living being, said controllable source of therapy radiation being arranged for providing at least one gamma or x ray or particulate therapy beam and being arranged for receipt of said electrical signal to precisely direct said at least one therapy beam to the living tumor tissue to which said radiopharmaceutical is attached, whereupon said at least one therapy beam necrotizes that tissue with minimal damage to adjacent viable tissue.

9. The system of claim 8 wherein said controllable source of therapy radiation comprises means to direct said at least one beam of said therapy radiation to the living tumor tissue to which the radiopharmaceutical has attached from plural directions.

10. The system of claim 9 wherein said controllable source of therapy radiation comprises means which produces a beam whose attributes is selectable.

11. The system of claim 8 wherein said radiopharmaceutical includes a radioactive isotope producing radiation therefrom prior to introduction into the body of the living being.

12. The system of claim 11 wherein said radiopharmaceutical is adapted to attach itself to the living tumor tissue.

13. A system for providing precise therapy radiation to living tumor tissue within the body of a living being provided with a tumor localizing radiopharmaceutical attached to the living tumor tissue, the radiopharmaceutical emitting gamma-ray photons, characteristic x-ray photons, and an associated continuum of Compton-scattered photons from the living tumor tissue to which said radiopharmaceutical is attached, said system comprising a controllable source of therapy radiation, and radiation detection means, said radiation detecting means being arranged to be brought into various positions adjacent the body of the being for detecting the characteristic x rays and the gamma rays from a plurality of directions to provide an indication of the three dimensional distribution of the living tumor tissue to which said radiopharmaceutical is attached and for providing an electrical signal indicating the three dimensional distribution of the living tumor tissue to which the radiopharmaceutical is attached, irrespective of the location thereof within the body of the living being, said controllable source of therapy radiation being arranged for providing at least one gamma or x ray or particulate therapy beam and being arranged for receipt of said electrical signal to precisely direct said at least one therapy beam to the living tumor tissue to which said radiopharmaceutical is attached to necrotize that tissue with minimal damage to adjacent viable tissue.

14. The system of claim 13 wherein said system includes first means to ensure that only minimal portions of said electrical signal represent Compton scattered photons.

15. The system of claim 14 wherein said first means includes removal means to substantially remove from said electrical signal portions which represent the Compton scattered photons received by said radiation detecting means.

16. The system of claim 13 wherein said radiopharmaceutical includes a radioactive isotope producing radiation therefrom prior to introduction into the body of the living being.

17. The system of claim 16 wherein said radiopharmaceutical is adapted to attach itself to the living tumor tissue.

18. The system of claim 1 wherein said radiation detecting means includes means for effecting at least one of the group consisting of fluroscopy, computed tomography imaging, and gamma ray imaging.

19. The system of claim 1 wherein said system comprises means for effecting isotope detection and computed tomography simultaneously for achieving optimal therapy beam guidance.

20. The system of claim 1 wherein said radiopharmaceutical includes a radioactive isotope producing radiation therefrom prior to introduction into the body of the living being.

21. The system of claim 20 wherein said radiopharmaceutical is adapted to attach itself to the living tumor tissue.

22. A system for providing precise therapy radiation to living tumor tissue within the body of a living being comprising a tumor localizing radiopharmaceutical, a controllable source of beam radiation, and radiation detection means, said tumor localizing radiopharmaceutical being radioactive prior to introduction into the body of the being and arranged for provision into the body of the living being for attachment to the living tumor tissue within the body of the being, whereupon said radiopharmaceutical provides tumor-localizing radiation from the living tumor tissue to which said radiopharmaceutical has attached, said tumor-localizing radiation comprising photons of different energies produced by said radiopharmaceutical, including gamma radiation, x radiation, and/or annihilation radiation, said radiation detecting means being arranged to be brought into various positions adjacent the body of the being for detecting said tumor localizing radiation from a plurality of directions and utilizing the known naturally occurring abundance of emitted photons of different energies of said radiopharmaceutical as a reference factor to provide an indication of the three dimensional distribution of the living tumor tissue to which said radiopharmaceutical has attached and for providing a signal indicative thereof, said controllable source of therapy radiation being arranged for receipt of said signal to precisely direct at least one beam of said therapy radiation to the living tumor tissue to which said radiopharmaceutical has attached, whereupon said at least one beam necrotizes that tissue with minimal damage to adjacent viable tissue.

23. The system of claim 22 wherein said controllable source of therapy radiation comprises means to direct said at least one beam of said therapy radiation to the living tumor tissue to which the radiopharmaceutical has attached from plural directions.

24. The system of claim 23 wherein said controllable source of therapy radiation comprises means which produces at least one beam of said therapy radiation whose energy is selectable.

25. The system of claim 24 wherein said means which produces said at least one beam of said therapy radiation is adjustable so that the energy of said at least one beam of said therapy radiation is a function of thickness and type of tissue intervening between it and the living tumor tissue to which the radiopharmaceutical has attached.

26. The system of claim 22 wherein said controllable source of therapy radiation comprises means which produces at least one beam of said therapy radiation whose attributes is selectable.

27. The system of claim 26 wherein said means which produces said at least one beam of said therapy radiation is adjustable so that the energy of said at least one beam of said therapy radiation is a function of thickness and type of tissue intervening between it and the living tumor tissue to which said radiopharmaceutical has attached.

28. The system of claim 22 wherein said controllable source of therapy radiation comprises means to precisely direct said at least one beam of said therapy radiation to the living tumor tissue to which said radiopharmaceutical has attached in automatic response to said signal.

29. The system of claim 22 wherein said radiopharmaceutical emits annihilation radiation and/or characteristic x rays and gamma rays, and wherein said radiation detecting means detects the annihilation radiation and/or the characteristic x rays and/or the gamma rays to provide said electrical signal indicating the three dimensional distribution of the living tumor tissue to which said radiopharmaceutical has attached, irrespective of the location thereof within the body of the living being.

30. The system of claim 29 wherein said controllable source of therapy radiation comprises means to direct the beam to the living tumor tissue to which said radiopharmaceutical has attached from plural directions.

31. The system of claim 30 where in said controllable source of therapy radiation comprises means which produces a beam whose energy is selectable.

32. The system of claim 22 wherein the radiopharmaceutical emits annihilation radiation and/or gamma-ray photons, characteristic x-ray photons, and an associated continuum of Compton-scattered photons, and wherein said radiation detecting means detects the annihilation radiation and/or the characteristic x rays and/or the gamma rays to provide said electrical signal indicating the three dimensional distribution of the living tumor tissue to which the radiopharmaceutical has attached, irrespective of the location thereof within the body of the living being.

33. The system of claim 32 wherein said system includes first means to ensure that only minimal portions of said electrical signal represent Compton scattered photons.

34. The system of claim 33 wherein said first means includes removal means to substantially remove from said electrical signal portions which represent the Compton scattered photons received by said radiation detecting means.

35. The system of claim 22 wherein said radiation detecting means includes means for effecting at least one of the group consisting of fluroscopy, computed tomography imaging, and gamma ray imaging.

36. The system of claim 22 wherein said system comprises means for effecting isotope detection and computed tomography simultaneously for achieving optimal therapy beam guidance.

37. A method of providing precise therapy radiation to living tumor tissue within the body of a living being from an external, controllable source of therapy beam radiation, said method comprising a tumor localizing radiopharmaceutical attached to the living tumor tissue within the body of the being, whereupon said radiopharmaceutical provides tumor-localizing radiation from that tissue, said tumor-localizing radiation comprising photons of different energies produced by said radiopharmaceutical, including gamma radiation, x radiation, and/or annihilation radiation, detecting said tumor-localizing radiation from a plurality of directions, utilizing the known naturally occurring abundance of emitted photons of different energies of said radiopharmaceutical as a reference factor to provide an indication of the three dimensional distribution of the living tumor tissue to which said radiopharmaceutical is attached, and utilizing said indication of the three dimensional distribution of the living tumor tissue to precisely direct at least one beam of said therapy radiation thereto, whereupon said at least one beam of therapy radiation necrotizes that tissue with minimal damage to adjacent viable tissue.

38. The method of claim 37 wherein the beam is directed to the living tumor tissue to which said radiopharmaceutical has attached from plural directions.

39. The method of claim 38 wherein the energy of the beam is selected as a function of thickness and type of intervening tissue.

40. The method of claim 38 wherein said precise direction of the beam is effected automatically.

41. The method of claim 37 wherein the energy of the beam is selected as a function of thickness and type of intervening tissue.

42. The method of claim 37 wherein said radiopharmaceutical emits annihilation radiation and/or characteristic x rays and gamma rays, and wherein said method additionally comprises detecting the annihilation radiation and/or the characteristic x rays and/or the gamma rays to provide said indication of the three dimensional distribution of the living tumor tissue to which said radiopharmaceutical has attached, irrespective of the location thereof within the body of the living being.

43. The method of claim 42 wherein the beam is directed to the living tumor tissue to which said radiopharmaceutical has attached from plural directions.

44. The method of claim 42 wherein the energy of the beam is selected as a function of thickness and type of intervening tissue.

45. The method of claim 43 wherein the energy of the beam is selected as a function of thickness and type of intervening tissue.

46. The method of claim 37 wherein said precise direction of the beam is effected automatically.

47. The method of claim 37 wherein said method comprises providing an electrical signal indicative of the three dimensional distribution of the living tumor tissue to which said radiopharmaceutical has attached, and wherein said precise directing of the beam of the therapy radiation to the living tumor tissue to which said radiopharmaceutical has attached is accomplished utilizing said electrical signal.

48. The method of claim 47 wherein said precise directing of the beam of the therapy radiation to the living tumor tissue to which said radiopharmaceutical has attached is accomplished in automatic response to said electrical signal.

49. The method of claim 37 wherein said tumor localizing radiation includes annihilation radiation and/or gamma-ray photons, characteristic x-ray photons, and an associated continuum of Compton-scattered photons, and wherein said method detects the annihilation radiation and/or the characteristic x rays and/or the gamma rays to indicate the three dimensional distribution of the living tumor tissue to which the radiopharmaceutical has attached and to provide an electrical signal representative thereof.

50. The method of claim 49 comprising the step of ensuring that only minimal portions of said electrical signal represent Compton scattered photons.

51. The method of claim 50 comprising the step of substantially removing from said electrical signal portions which represent the Compton scattered photons which are detected.

52. The method of claim 37 wherein said detecting step is accomplished by radiation detecting means, said radiation detecting means being arranged for effecting at least one of the group consisting of fluroscopy, computed tomography imaging, and gamma ray imaging.

53. The method of claim 47 comprising effecting isotope detection and computed tomography simultaneously for achieving optimal therapy beam guidance.

54. The method of claim 37 wherein said radiopharmaceutical includes a radioactive isotope producing radiation therefrom prior to introduction into the body of the living being.

55. The method of claim 54 wherein said radiopharmaceutical is introduced into the body of the being so that said radiopharmaceutical attaches to the living tumor tissue.

\* \* \* \* \*